United States Patent
Dinsmore et al.

[11] Patent Number: 6,001,835
[45] Date of Patent: Dec. 14, 1999

[54] INHIBITORS OF FARNESYL-PROTEIN TRANSFERASE

[75] Inventors: Christopher J. Dinsmore, Schwenksville; Theresa M. Williams, Harleysville, both of Pa.

[73] Assignee: Merck & Co., Inc., Rahway, N.J.

[21] Appl. No.: 08/823,929

[22] Filed: Mar. 25, 1997

Related U.S. Application Data

[60] Provisional application No. 60/014,798, Apr. 3, 1996.

[51] Int. Cl.$^6$ .................. A01N 43/60; C07D 403/00; C07D 403/02; C07D 401/00
[52] U.S. Cl. .................. 514/255; 514/326; 514/397; 544/372; 544/386; 544/387; 544/388; 544/391; 544/395; 546/207; 546/210; 548/314.7
[58] Field of Search .................. 544/372, 395, 544/386, 387, 388, 391; 514/255, 326, 397; 546/210, 207; 548/314.7

[56] References Cited

U.S. PATENT DOCUMENTS

| | | | |
|---|---|---|---|
| 5,015,653 | 5/1991 | Olson | 514/397 |
| 5,055,467 | 10/1991 | Albaugh | 514/235.8 |
| 5,073,671 | 12/1991 | Weber et al. | 548/348 |
| 5,159,083 | 10/1992 | Thurkauf et al. | 548/335.5 |
| 5,371,101 | 12/1994 | Itoh et al. | 514/383 |
| 5,384,319 | 1/1995 | Ferrini | 544/372 |
| 5,576,313 | 11/1996 | Fisher et al. | 514/211 |

FOREIGN PATENT DOCUMENTS

| | | | |
|---|---|---|---|
| 0 102 227 | 3/1984 | European Pat. Off. . | |
| 0 175 187 | 3/1986 | European Pat. Off. . | |
| 284359 | 9/1988 | European Pat. Off. | 544/372 |
| 0 429 232 | 5/1991 | European Pat. Off. . | |
| 48-28679 | 10/1974 | Japan . | |
| WO 96/30017 | 10/1996 | WIPO . | |
| WO 96/31501 | 10/1996 | WIPO . | |
| WO96/30343 | 10/1996 | WIPO . | |
| WO96/37204 | 10/1996 | WIPO . | |

OTHER PUBLICATIONS

Smith et al, Chemical Abstract vol. 120 No. 217238, "Conversion of amides & lactams to thioamides & thiolactams" (1994).

Cabini et al, Chemical Abstract vol. 87 No. 23726, "Apparent molal heat cap. in aq. sol. of mol. containing peptide linkage." (1977).

Neville et al, Chemical Abstract vol. 126 No. 8133 "Prep. of piperazine & homopiperazine inhibitors of farnesyl–protein transferase" (1991).

Exp. Opin. Ther. Patents, vol. 5(12), pp. 1269–1285 (1995), by S. L. Graham.

Exp. Opin. Ther. Patents, vol. 6(12) (1996), pp. 12951304, by S. L. Graham, et al.

J. of Biol. Chem., vol. 269, No. 44, pp. 27706–27714 (1994), by G. L. James, et al.

J. of Biol. Chem., vol. 270, No. 11, pp. 6221–6226 (1995), by G. L. James, et al.

Science, vol. 260, pp. 1934–1937 (1993), by N. E. Kohl, et al.

Proc. Natl. Acad. Sci. USA, vol. 91, pp. 9141–9145 (1994), by N. E. Kohl, et al.

Nature Medicine, vol. 1, No. 8, pp. 792–797 (1995), by N. E. Kohl, et al.

Cancer Research, vol. 55, pp. 5302–5309 (1995), by L. Sepp–Lorenzino, et al.

*Primary Examiner*—John Kight
*Assistant Examiner*—Raymond Covington
*Attorney, Agent, or Firm*—Dianne Pecoraro; David A. Muthard; Mark R. Daniel

[57] ABSTRACT

The present invention is directed to compounds which inhibit farnesyl-protein transferase (FTase) and the farnesylation of the oncogene protein Ras. The invention is further directed to chemotherapeutic compositions containing the compounds of this invention and methods for inhibiting farnesyl-protein transferase and the farnesylation of the oncogene protein Ras.

29 Claims, No Drawings

INHIBITORS OF FARNESYL-PROTEIN TRANSFERASE

DOMESTIC PRIORITY CLAIM

The priority of U.S. Provisional Application Ser. No. 60/014,798, filed on Apr. 3, 1996, now abandoned, is claimed.

BACKGROUND OF THE INVENTION

The Ras proteins (Ha-Ras, Ki4a-Ras, Ki4b-Ras and N-Ras) are part of a signalling pathway that links cell surface growth factor receptors to nuclear signals initiating cellular proliferation. Biological and biochemical studies of Ras action indicate that Ras functions like a G-regulatory protein. In the inactive state, Ras is bound to GDP. Upon growth factor receptor activation Ras is induced to exchange GDP for GTP and undergoes a conformational change. The GTP-bound form of Ras propagates the growth stimulatory signal until the signal is terminated by the intrinsic GTPase activity of Ras, which returns the protein to its inactive GDP bound form (D. R. Lowy and D. M. Willumsen, *Ann. Rev. Biochem.* 62:851–991 (1993)). Mutated ras genes (Ha-ras, Ki4a-ras, Ki4b-ras and N-ras) are found in many human cancers, including colorectal carcinoma, exocrine pancreatic carcinoma, and myeloid leukemias. The protein products of these genes are defective in their GTPase activity and constitutively transmit a growth stimulatory signal.

Ras must be localized to the plasma membrane for both normal and oncogtenic functions. At least 3 post-translational modifications are involved with Ras membrane localization, and all 3 modifications occur at the C-terminus of Ras. The Ras C-terminus contains a sequence motif termed a "CAAX" or "Cys-Aaa$^1$-Aaa$^2$-Xaa" box (Cys is cysteine, Aaa is an aliphatic amino acid, the Xaa is any amino acid) (Willumsen et al., *Nature* 310:583–586 (1984)). Depending on the specific sequence, this motif serves as a signal sequence for the enzymes farnesyl-protein transferase or geranylgeranyl-protein transferase, which catalyze the alkylation of the cysteine residue of the CAAX motif with a $C_{15}$ or $C_{20}$ isoprenoid, respectively. (S. Clarke., *Ann. Rev. Biochem.* 61:355–386 (1992); W. R. Schafer and J. Rine, *Ann. Rev. Genetics* 30:209–237 (1992)). The Ras protein is one of several proteins that are known to undergo post-translational farnesylation. Other farnesylated proteins include the Ras-related GTP-binding proteins such as Rho, fungal mating factors, the nuclear lamins, and the gamma subunit of transducin. James, et al., *J. Biol. Chem.* 269, 14182 (1994) have identified a peroxisome associated protein Pxf which is also farnesylated. James, et al., have also suggested that there are farnesylated proteins of unknown structure and function in addition to those listed above.

Inhibition of farnesyl-protein transferase has been shown to block the growth of Ras-transformed cells in soft agar and to modify other aspects of their transformed phenotype. It has also been demonstrated that certain inhibitors of farnesyl-protein transferase selectively block the processing of the Ras oncoprotein intracellularly (N. E. Kohl et al., *Science,* 260:1934–1937 (1993) and G. L. James et al., *Science,* 260:1937–1942 (1993). Recently, it has been shown that an inhibitor of farnesyl-protein transferase blocks the growth of ras-dependent tumors in nude mice (N. E. Kohl et al., *Proc. Natl. Acad. Sci U.S.A.,* 91:9141–9145 (1994) and induces regression of mammary and -salivary carcinomas in ras transgenic mice (N. E. Kohl et al., *Nature—Medicine,* 1:792–797 (1995).

Indirect inhibition of farnesyl-protein transferase in vivo has been demonstrated with lovastatin (Merck & Co., Rahway, N.J.) and compactin (Hancock et al., ibid; Casey et al., ibid; Schafer et al., *Science* 245:379 (1989)). These drugs inhibit HMG-CoA reductase, the rate limiting enzyme for the production of polyisoprenoids including farnesyl pyrophosphate. Farnesyl-protein transferase utilizes farnesyl pyrophosphate to covalently modify the Cys thiol group of the Ras CAAX box with a farnesyl group (Reiss et al., *Cell,* 62:81–88 (1990); Schaber et al., *J. Biol. Chem.,* 265:14701–14704 (1990); Schafer et al., *Science,* 249:1133–1139 (1990); Manne et al., *Proc. Natl. Acad. Sci USA,* 87:7541–7545 (1990)). Inhibition of farnesyl pyrophosphate biosynthesis by inhibiting HMG-CoA reductase blocks Ras membrane localization in cultured cells. However, direct inhibition of farnesyl-protein transferase would be more specific and attended by fewer side effects than would occur with the required dose of a general inhibitor of isoprene biosynthesis.

Inhibitors of farnesyl-protein transferase (FPTase) have been described in two general classes. The first are analogs of farnesyl diphosphate (FPP), while the second class of inhibitors is related to the protein substrates (e.g., Ras) for the enzyme. The peptide derived inhibitors that have been described are generally cysteine containing molecules that are related to the CAAX motif that is the signal for protein prenylation. (Schaber et al., ibid; Reiss et. al., ibid; Reiss et al., *PNAS,* 88:732–736 (1991)). Such inhibitors may inhibit protein prenylation while serving as alternate substrates for the farnesyl-protein transferase enzyme, or may be purely competitive inhibitors (U.S. Pat. No. 5,141,851, University of Texas; N. E. Kohl et al., *Science,* 260:1934–1937 (1993); Graham, et al., *J. Med. Chem.,* 37, 725 (1994)). In general, deletion of the thiol from a CAAX derivative has been shown to dramatically reduce the inhibitory potency of the compound. However, the thiol group potentially places limitations on the therapeutic application of FPTase inhibitors with respect to pharmacokinetics, pharmacodynamics and toxicity. Therefore, a functional replacement for the thiol is desirable.

It has recently been reported that farnesyl-protein transferase inhibitors are inhibitors of proliferation of vascular smooth muscle cells and are therefore useful in the prevention and therapy of arteriosclerosis and diabetic disturbance of blood vessels (JP H7-112930).

It has recently been disclosed that certain tricyclic compounds which optionally incorporate a piperidine moiety are inhibitors of FPTase (WO 95/10514, WO 95/10515 and WO 95/10516). Imidazole-containing inhibitors of farnesyl protein transferase have also been disclosed (WO 95/09001 and EP 0 675 112 A1).

It is, therefore, an object of this invention to develop peptidomimetic compounds that do not have a thiol moiety, and that will inhibit farnesyl-protein transferase and thus, the post-translational farnesylation of proteins. It is a further object of this invention to develop chemotherapeutic compositions containing the compounds of this invention and methods for producing the compounds of this invention.

SUMMARY OF THE INVENTION

The present invention comprises peptidomimetic piperazine-containing compounds which inhibit the farnesyl-protein transferase. The instant compounds lack a thiol moiety and thus offer unique advantages in terms of improved pharmacokinetic behavior in animals, prevention of thiol-dependent chemical reactions, such as rapid autoxidation and disulfide formation with endogenous thiols, and reduced systemic toxicity. Further contained in this invention are chemotherapeutic compositions containing these farnesyl transferase inhibitors and methods for their production.

The compounds of this invention are illustrated by the formula A:

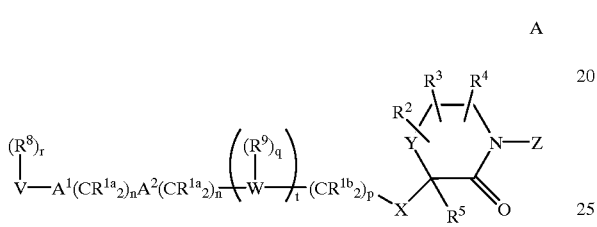

A

DETAILED DESCRIPTION OF THE INVENTION

The compounds of this invention are useful in the inhibition of farnesyl-protein transferase and the farnesylation of the oncogene protein Ras. In a first embodiment of this invention, the inhibitors of farnesyl-protein transferase are illustrated by the formula A:

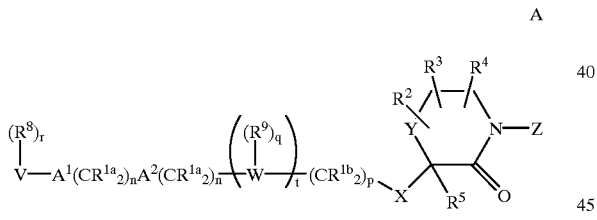

A wherein:
$R^{1a}$ and $R^{1b}$ are independently selected from:
  a) hydrogen,
  b) aryl, heterocycle, $C_3$–$C_{10}$ cycloalkyl, $C_2$–$C_6$ alkenyl, $C_2$–$C_6$ alkynyl, $R^{10}O$—, $R^{11}S(O)_m$—, $R^{10}C(O)NR^{10}$—, $CN(R^{10})_2NC(O)$—, $R^{10}{}_2N$—$C(NR^{10})$—, CN, $NO_2$, $R^{10}C(O)$—, $N_3$, —$N(R^{10})_2$, or $R^{11}OC(O)NR^{10}$—,
  c) unsubstituted or substituted $C_1$–$C_6$ alkyl wherein the substitutent on the substituted $C_1$–$C_6$ alkyl is selected from unsubstituted or substituted aryl, heterocyclic, $C_3$–$C_{10}$ cycloalkyl, $C_2$–$C_6$ alkenyl, $C_2$–$C_6$ alkynyl, $R^{10}O$—, $R^{11}S(O)_m$—, $R^{10}C(O)NR^{10}$—, $(R^{10})_2NC(O)$—, $R^{10}{}_2N$—$C(NR^{10})$—, CN, $R^{10}C(O)$—, $N_3$, —$N(R^{10})_2$, and $R^{11}C(O)$—$NR^{10}$—;
$R^2$ and $R^4$ are independently selected from: H; unsubstituted or substituted $C_{1-8}$ alkyl, unsubstituted or substituted $C_{2-8}$ alkenyl, unsubstituted or substituted $C_{2-8}$ alkynyl, unsubstituted or substituted aryl, unsubstituted or substituted heterocycle,

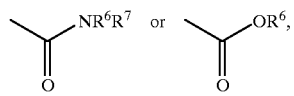

wherein the substituted group is substituted with one or more of:
  1) aryl or heterocycle, unsubstituted or substituted with:
    a) $C_{1-4}$ alkyl,
    b) $(CH_2)_pOR^6$,
    c) $(CH_2)_pNR^6R^7$,
    d) halogen,
    e) CN,
    f) aryl or heteroaryl,
    g) perfluoro-$C_{1-4}$ alkyl,
    h) $SR^{6a}$, $S(O)R^{6a}$, $SO_2R^{6a}$,
  2) $C_{3-6}$ cycloalkyl,
  3) $OR^6$,
  4) $SR^{6a}$, $S(O)R^{6a}$, or $SO_2R^{6a}$,

5)
  —$NR^6R^7$,

6)
  $$-\!\!-\!\!N(R^6)\!-\!\!C(O)\!-\!R^7,$$

7)
  $$-\!\!-\!\!N(R^6)\!-\!\!C(O)\!-\!NR^7R^{7a},$$

8)
  $$-\!\!-\!\!O\!-\!\!C(O)\!-\!NR^6R^7,$$

9)
  $$-\!\!-\!\!O\!-\!\!C(O)\!-\!OR^6,$$

10)
  $$\text{-C(O)}NR^6R^7,$$

11)
  —$SO_2$—$NR^6R^7$,

12)
  $$-\!\!-\!\!N(R^6)\!-\!\!SO_2\!-\!R^{6a},$$

13)
  $$\text{-C(O)}R^6,$$

14)
  $$\text{-C(O)}OR^6,$$

-continued

15) N₃,

16) F, or 17) perfluoro-$C_{1-4}$-alkyl; or $R^3$ and $R^5$ are selected from H and $CH_3$;

$R^2$ and $R^3$ or $R^4$ and $R^5$ are attached to the same C atom and are combined to form $-(CH_2)_u-$ wherein one of the carbon atoms is optionally replaced by a moiety selected from: O, $S(O)_m$, $-NC(O)-$, and $-N(COR^{10})-$;

$R^6$, $R^7$ and $R^{7a}$ are independently selected from: H; $C_{1-4}$ alkyl, $C_{3-6}$ cycloalkyl, heterocycle, aryl, aroyl, heteroaroyl, arylsulfonyl, heteroarylsulfonyl, unsubstituted or substituted with:
 a) $C_{1-4}$ alkoxy,
 b) aryl or heterocycle,
 c) halogen,
 d) HO,
 e)

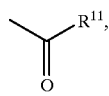

f) $-SO_2R^{11}$, or
 g) $N(R^{10})_2$; or $R^6$ and $R^7$ may be joined in a ring;
$R^7$ and $R^{7a}$ may be joined in a ring;
$R^{6a}$ is selected from: $C_{1-4}$ alkyl, $C_{3-6}$ cycloalkyl, heterocycle, aryl, unsubstituted or substituted with:
 a) $C_{1-4}$ alkoxy,
 b) aryl or heterocycle,
 c) halogen,
 d) HO,
 e)

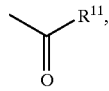

f) $-SO_2R^{11}$ or
 g) $N(R^{10})_2$;

$R^8$ is independently selected from:
 a) hydrogen,
 b) aryl, heterocycle, $C_3-C_{10}$ cycloalkyl, $C_2-C_6$ alkenyl, $C_2-C_6$ alkynyl, perfluoroalkyl, F, Cl, Br, $R^{10}O-$, $R^{11}S(O)_m-$, $R^{10}C(O)NR^{10}-$, $(R^{10})_2NC(O)-$, $R^{10}{}_2N-C(NR^{10})-$, CN, $NO_2$, $R^{10}C(O)-$, $N_3$, $-N(R^{10})_2$, or $R^{11}OC(O)NR^{10}-$, and
 c) $C_1-C_6$ alkyl unsubstituted or substituted by aryl, cyanophenyl, heterocycle, $C_3-C_{10}$ cycloalkyl, $C_2-C_6$ alkenyl, $C_2-C_6$ alkynyl, perfluoroalkyl, F, Cl, Br, $R^{10}O-$, $R^{11}S(O)_m-$, $R^{10}C(O)NH-$, $(R^{10})_2NC(O)-$, $R^{10}{}_2N-C(NR^{10})-$, CN, $R^{10}C(O)-$, $N_3$, $-N(R^{10})_2$, or $R^{10}OC(O)NH-$;

$R^9$ is selected from:
 a) hydrogen,
 b) alkenyl, alkynyl, perfluoroalkyl, F, Cl, Br, $R^{10}O-$, $R^{11}S(O)_m-$, $R^{10}C(O)NR^{10}-$, $(R^{10})_2NC(O)-$, $R^{10}{}_2N-C(NR^{10})-$, CN, $NO_2$, $R^{10}C(O)-$, $N_3$, $-N(R^{10})_2$, or $R^{11}OC(O)NR^{10}-$, and
 c) $C_1-C_6$ alkyl unsubstituted or substituted by perfluoroalkyl, F, Cl, Br, $R^{10}O-$, $R^{11}S(O)_{m-}$, $R^{10}C(O)NR^{10}-$, $(R^{10})_2NC(O)-$, $R^{10}{}_2N-C(NR^{10})-$, CN, $R^{10}C(O)-$, $N_3$, $-N(R^{10})_2$, or $R^{11}OC(O)NR^{10}-$;

$R^{10}$ is independently selected from hydrogen, $C_1-C_6$ alkyl, benzyl and aryl;

$R^{11}$ is independently selected from $C_1-C_6$ alkyl and aryl;

$A^1$ and $A^2$ are independently selected from: a bond, $-CH=CH-$, $-C\equiv C-$, $-C(O)-$, $-C(O)NR^{10}-$, $-NR^{10}C(O)-$, O, $-N(R^{10})-$, $-S(O)_2N(R^{10})-$, $-N(R^{10})S(O)_2-$, or $S(O)_m$;

V is selected from:
 a) hydrogen,
 b) heterocycle,
 c) aryl,
 d) $C_1-C_{20}$ alkyl wherein from 0 to 4 carbon atoms are replaced with a a heteroatom selected from O, S, and N, and
 e) $C_2-C_{20}$ alkenyl, provided that V is not hydrogen if $A^1$ is $S(O)_m$ and V is not hydrogen if $A^1$ is a bond, n is 0 and $A^2$ is $S(O)_m$;

W is a heterocycle;
X is a bond, $-CH_2-$, $-C(=O)-$, $-C(O)NR^6-$, $-NR^6C(O)-$, $-NR^6-$ or $-S(=O)_m-$;
Y is a bond, $-CH_2-$, $-NH-$, $-S(=O)_m-$ or O;
Z is selected from:
 1) a unsubstituted or substituted group selected from aryl, heteroaryl, arylmethyl, heteroarylmethyl, arylsulfonyl, heteroarylsulfonyl, wherein the substituted group is substituted with one or more of the following:
  a) $C_{1-4}$ alkyl, unsubstituted or substituted with: $C_{1-4}$ alkoxy, $NR^6R^7$, $C_{3-6}$ cycloalkyl, aryl, heterocycle, HO, $-S(O)_mR^{6a}$, or $-C(O)NR^6R^7$,
  b) aryl or heterocycle,
  c) halogen,
  d) $OR^6$,
  e) $NR^6R^7$,
  f) CN,
  g) $NO_2$,
  h) $CF_3$;
  i) $-S(O)_mR^{6a}$,
  j) $-C(O)NR^6R^7$, or
  k) $C_3-C_6$ cycloalkyl; or
 2) unsubstituted $C_1-C_6$ alkyl, substituted $C_1-C_6$ alkyl, unsubstituted $C_3-C_6$ cycloalkyl or substituted $C_3-C_6$ cycloalkyl, wherein the substituted $C_1-C_6$ alkyl and substituted $C_3-C_6$ cycloalkyl is substituted with one or two of the following:
  a) $C_{1-4}$ alkoxy,
  b) $NR^6R^7$,
  c) $C_{3-6}$ cycloalkyl,
  d) $-NR^6C(O)R^7$,
  e) HO,
  f) $-S(O)_mR^{6a}$,
  g) halogen, or
  h) perfluoroalkyl;

m is 0, 1 or 2;
n is 0, 1, 2, 3 or 4;
p is 0, 1, 2, 3 or 4;
q is 1 or 2;
r is 0 to 5, provided that r is 0 when V is hydrogen;
t is 0 or 1; and
u is 4 or 5;
or the pharmaceutically acceptable salts thereof.

A preferred embodiment of the compounds of this invention is illustrated by the following formula:

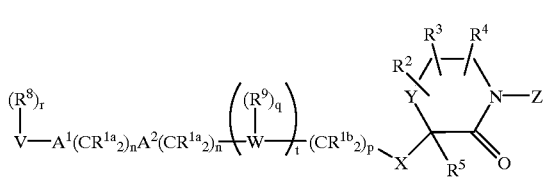

A wherein:

$R^{1a}$ is independently selected from: hydrogen or $C_1$–$C_6$ alkyl;

$R^{1b}$ is independently selected from:
a) hydrogen,
b) aryl, heterocycle, cycloalkyl, $R^{10}O$—, —$N(R^{10})_2$ or $C_2$–$C_6$ alkenyl,
c) unsubstituted or substituted $C_1$–$C_6$ alkyl wherein the substitutent on the substituted $C_1$–$C_6$ alkyl is selected from unsubstituted or substituted aryl, heterocycle, cycloalkyl, alkenyl, $R^{10}O$— and —$N(R^{10})_2$;

$R^3$ and $R^5$ are independently selected from H and $CH_3$;

$R^2$ and $R^4$ are independently selected from H;

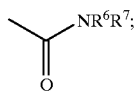

$C_{1-5}$ alkyl, unbranched or branched, unsubstituted or substituted with one or more of:
1) aryl,
2) heterocycle,
3) $OR^6$,
4) $SR^{6a}$, $SO_2R^{6a}$, or
5)

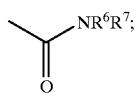

and any two of $R^2$, $R^3$, $R^4$, and $R^5$ are optionally attached to the same carbon atom;

$R^6$, $R^7$ and $R^{7a}$ are independently selected from:
H; $C_{1-4}$ alkyl, $C_{3-6}$ cycloalkyl, aryl, heterocycle, unsubstituted or substituted with:
a) $C_{1-4}$ alkoxy,
b) halogen, or
c) aryl or heterocycle;

$R^{6a}$ is selected from:
$C_{1-4}$ alkyl or $C_{3-6}$ cycloalkyl, unsubstituted or substituted with:
a) $C_{1-4}$ alkoxy,
b) halogen, or
c) aryl or heterocycle;

$R^8$ is independently selected from:
a) hydrogen,
b) $C_1$–$C_6$ alkyl, $C_2$–$C_6$ alkenyl, $C_2$–$C_6$ alkynyl, $C_1$–$C_6$ perfluoroalkyl, F, Cl, $R^{10}O$—, $R^{10}C(O)NR^{10}$—, CN, $NO_2$, $(R^{10})_2N$—$C(NR^{10})$—, $R^{10}C(O)$—, —$N(R^{10})_2$, or $R^{11}OC(O)NR^{10}$—, and
c) $C_1$–$C_6$ alkyl substituted by $C_1$–$C_6$ perfluoroalkyl, $R^{10}O$—, $R^{10}C(O)NR^{10}$—, $(R^{10})_2N$—$C(NR^{10})$—, $R^{10}C(O)$—, —$N(R^{10})_2$, or $R^{11}OC(O)NR^{10}$—;

$R^9$ is selected from:
a) hydrogen,
b) $C_2$–$C_6$ alkenyl, $C_2$–$C_6$ alkynyl, $C_1$–$C_6$ perfluoroalkyl, F, Cl, $R^{10}O$—, $R^{11}S(O)_m$—, $R^{10}C(O)NR^{10}$—, CN, $NO_2$, $(R^{10})_2N$—$C(NR^{10})$—, $R^{10}C(O)$—, —$N(R^{10})_2$, or $R^{11}OC(O)NR^{10}$—, and
c) $C_1$–$C_6$ alkyl unsubstituted or substituted by $C_1$–$C_6$ perfluoroalkyl, F, Cl, $R^{10}O$—, $R^{11}S(O)_m$—, $R^{10}C(O)NR^{10}$—, CN, $(R^{10})_2N$—$C(NR^{10})$—, $R^{10}C(O)$—, —$N(R^{10})_2$, or $R^{11}OC(O)NR^{10}$—;

$R^{10}$ is independently selected from hydrogen, $C_1$–$C_6$ alkyl, benzyl and aryl;

$R^{11}$ is independently selected from $C_1$–$C_6$ alkyl and aryl;

$A^1$ and $A^2$ are independently selected from: a bond, —CH=CH—, —C≡C—, —C(O)—, —C(O)$NR^{10}$—, O, —$N(R^{10})$—, or $S(O)_m$;

V is selected from:
a) hydrogen,
b) heterocycle selected from pyrrolidinyl, imidazolyl, pyridinyl, thiazolyl, pyridonyl, 2-oxopiperidinyl, indolyl, quinolinyl, isoquinolinyl, and thienyl,
c) aryl,
d) $C_1$–$C_{20}$ alkyl wherein from 0 to 4 carbon atoms are replaced with a a heteroatom selected from O, S, and N, and
e) $C_2$–$C_{20}$ alkenyl, and provided that V is not hydrogen if $A^1$ is $S(O)_m$ and V is not hydrogen if $A^1$ is a bond, n is 0 and $A^2$ is $S(O)_m$;

W is a heterocycle selected from pyrrolidinyl, imidazolyl, pyridinyl, thiazolyl, pyridonyl, 2-oxopiperidinyl, indolyl, quinolinyl, or isoquinolinyl;

X is —$CH_2$— or —C(=O)—;

Y is a bond or —$CH_2$—;

Z is selected from:
1) a unsubstituted or substituted group selected from aryl, heteroaryl, arylmethyl, heteroarylmethyl, arylsulfonyl, heteroarylsulfonyl, wherein the substituted group is substituted with one or more of the following:
a) $C_{1-4}$ alkyl, unsubstituted or substituted with: $C_{1-4}$ alkoxy, $NR^6R^7$, $C_{3-6}$ cycloalkyl, aryl, heterocycle, HO, —$S(O)_mR^{6a}$, or —$C(O)NR^6R^7$,
b) aryl or heterocycle,
c) halogen,
d) $OR^6$,
e) $NR^6R^7$,
f) CN,
g) $NO_2$,
h) $CF_3$,
i) —$S(O)_mR^{6a}$,
j) —$C(O)NR^6R^7$, or
k) $C_3$–$C_6$ cycloalkyl; or
2) unsubstituted $C_1$–$C_6$ alkyl, substituted $C_1$–$C_6$ alkyl, unsubstituted $C_3$–$C_6$ cycloalkyl or substituted $C_3$–$C_6$ cycloalkyl, wherein the substituted $C_1$–$C_6$ alkyl and substituted $C_3$–$C_6$ cycloalkyl is substituted with one or two of the following:
a) $C_{1-4}$ alkoxy,
b) $NR^6R^7$,
c) $C_{3-6}$ cycloalkyl,
d) —$NR^6C(O)R^7$,
e) HO,
f) —$S(O)_mR^{6a}$, g) halogen, or h) perfluoroalkyl;

m is 0, 1 or 2;

n is 0, 1, 2, 3 or 4;

p is 0, 1, 2, 3 or 4;

r is 0 to 5, provided that r is 0 when V is hydrogen;

t is 0 or 1; and u is 4 or 5;

or the pharmaceutically acceptable salts thereof.

A preferred embodiment of the compounds of this invention are illustrated by the formula B:

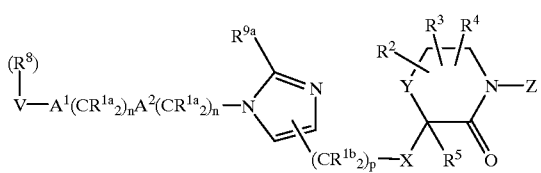

B wherein:

$R^{1a}$ is selected from: hydrogen or $C_1$–$C_6$ alkyl; $R^{1b}$ is independently selected from:

a) hydrogen, b) aryl, heterocycle, cycloalkyl, $R^{10}O$—, —$N(R^{10})_2$ or $C_2$–$C_6$ alkenyl, c) $C_1$–$C_6$ alkyl unsubstituted or substituted by aryl, heterocycle, cycloalkyl, alkenyl, $R^{10}O$—, or —$N(R^{10})_2$;

$R^3$ and $R^5$ are independently selected from H and $CH_3$;

$R^2$ and $R^4$ are independently selected from H;

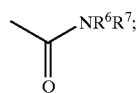

or $C_{1-5}$ alkyl, unbranched or branched, unsubstituted or substituted with one or more of:

1) aryl, 2) heterocycle,

3) $OR^6$,

4) $SR^{6a}$, $SO_2R^{6a}$, or

5)

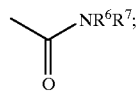

and any two of $R^2$, $R^3$, $R^4$, and $R^5$ are optionally attached to the same carbon atom;

$R^6$ and $R^7$ are independently selected from:

a) hydrogen, b) $C_1$–$C_6$ alkyl, $C_2$–$C_6$ alkenyl, $C_2$–$C_6$ alkynyl, $C_1$–$C_6$ perfluoroalkyl, F, Cl, $R^{10}O$—, $R^{10}C(O)NR^{10}$—, CN, $NO_2$, $(R^{10})_2N$—$C(NR^{10})$—, $R^{10}C(O)$—, $R^{10}OC(O)$—, —$N(R^{10})_2$, or $R^{11}OC(O)NR^{10}$—, and c) $C_1$–$C_6$ alkyl substituted by $C_1$–$C_6$ perfluoroalkyl, $R^{10}O$—, $R^{10}C(O)NR^{10}$, $(R^{10})_2N$—$C(NR^{10})$—, $R^{10}C(O)$—, $R^{10}C(O)$—, —$N(R^{10})_2$, or $R^{11}OC(O)NR^{10}$—;

$R^{6a}$ is selected from:

$C_{1-4}$ alkyl or $C_{3-6}$ cycloalkyl, unsubstituted or substituted with:

a) $C_{1-4}$ alkoxy, b) halogen, or c) aryl or heterocycle;

$R^8$ is independently selected from:

a) hydrogen, b) $C_1$–$C_6$ alkyl, $C_2$–$C_6$ alkenyl, $C_2$–$C_6$ alkynyl, $C_1$–$C_6$ perfluoroalkyl, F, Cl, $R^{10}O$—, $R^{10}C(O)NR^{10}$—, CN, $NO_2$, $(R^{10})_2N$—$C(NR^{10})$—, $R^{11}C(O)$—, —$N(R^{10})_2$, or $R^{10}OC(O)NR^{10}$—, and c) $C_1$–$C_6$ alkyl substituted by $C_1$–$C_6$ perfluoroalkyl, $R^{10}O$—, $R^{10}C(O)NR^{10}$—, $(R^{10})_2N$—$C(NR^{10})$—, $R^{11}C(O)$—, —$N(R^{10})_2$, or $R^{11}OC(O)NR^{10}$—;

$R^{9a}$ is hydrogen or methyl;

$R^{10}$ is independently selected from hydrogen, $C_1$–$C_6$ alkyl, benzyl and aryl;

$R^{11}$ is independently selected from $C_1$–$C_6$ alkyl and aryl;

$A^1$ and $A^2$ are independently selected from: a bond, —CH=CH—, —C≡C—, —C(O)—, —C(O)$NR^{10}$—, O, —$N(R^{10})$—, or $S(O)_m$;

V is selected from:

a) hydrogen, b) heterocycle selected from pyrrolidinyl, imidazolyl, pyridinyl, thiazolyl, pyridonyl, 2-oxopiperidinyl, indolyl, quinolinyl, isoquinolinyl, and thienyl, c) aryl, d) $C_1$–$C_{20}$ alkyl wherein from 0 to 4 carbon atoms are replaced with a a heteroatom selected from O, S, and N, and e) $C_2$–$C_{20}$ alkenyl, and provided that V is not hydrogen if $A^1$ is $S(O)_m$ and V is not hydrogen if $A^1$ is a bond, n is 0 and $A^2$ is $S(O)_m$;

X is —$CH_2$— or —C(=O)—;

Y is a bond, —$CH_2$—, —NH—, —S(=O)$_m$— or O;

Z is selected from:

1) a unsubstituted or substituted group selected from aryl, heteroaryl, arylmethyl, heteroarylmethyl, arylsulfonyl, heteroarylsulfonyl, wherein the substituted group is substituted with one or more of the following:

a) $C_{1-4}$ alkyl, unsubstituted or substituted with: $C_{1-4}$ alkoxy, $NR^6R^7$, $C_{3-6}$ cycloalkyl, aryl, heterocycle, HO, —$S(O)_mR^{6a}$, or —$C(O)NR^6R^7$, b) aryl or heterocycle, c) halogen, d) $OR^6$, e) $NR^6R^7$, f) CN, g) $NO_2$, h) $CF_3$;

i) —$S(O)_mR^{6a}$, j) —$C(O)NR^6R^7$, or k) $C_3$–$C_6$ cycloalkyl; or 2) unsubstituted $C_1$–$C_6$ alkyl, substituted $C_1$–$C_6$ alkyl, unsubstituted $C_3$–$C_6$ cycloalkyl or substituted $C_3$–$C_6$ cycloalkyl, wherein the substituted $C_1$–$C_6$ alkyl and substituted $C_3$–$C_6$ cycloalkyl is substituted with one or two of the following:

a) $C_{1-4}$ alkoxy, b) $NR^6R^7$, c) $C_{3-6}$ cycloalkyl, d) —$NR^6C(O)R^7$, e) HO, f) —$S(O)_mR^{6a}$, g) halogen, or h) perfluoroalkyl;

m is 0, 1 or 2;
n is 0, 1, 2, 3 or 4;
p is 0, 1, 2, 3 or 4; and
r is 0 to 5, provided that r is 0 when V is hydrogen;
or the pharmaceutically acceptable salts thereof.

In a more preferred embodiment of this invention, the inhibitors of farnesyl-protein transferase are illustrated by the formula C:

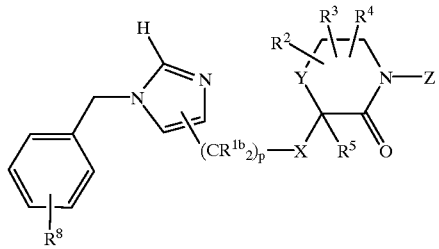

wherein:
$R^{1b}$ is independently selected from:
a) hydrogen,
b) aryl, heterocycle, cycloalkyl, $R^{10}O-$, $-N(R^{10})_2$ or $C_2-C_6$ alkenyl,
c) $C_1-C_6$ alkyl unsubstituted or substituted by aryl, heterocycle, cycloalkyl, alkenyl, $R^{10}O-$, or $-N(R^{10})_2$;
$R^3$ and $R^5$ are independently selected from H and $CH_3$;
$R^2$ and $R^4$ are independently selected from H;

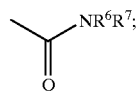

or $C_{1-5}$ alkyl, unbranched or branched, unsubstituted or substituted with one or more of:
1) aryl,
2) heterocycle,
3) $OR^6$,
4) $SR^{6a}$, $SO_2R^{6a}$, or
5)

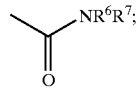

and any two of $R^2$, $R^3$, $R^4$, and $R^5$ are optionally attached to the same carbon atom;
$R^6$ and $R^7$ are independently selected from:
a) hydrogen,
b) $C_1-C_6$ alkyl, $C_2-C_6$ alkenyl, $C_2-C_6$ alkynyl, $C_1-C_6$ perfluoroalkyl, F, Cl, $R^{10}O-$, $R^{10}C(O)NR^{10}-$, CN, $NO_2$, $(R^{10})_2N-C(NR^{10})-$, $R^{10}C(O)-$, $R^{10}OC(O)-$, $-N(R^{10})_2$, or $R^{11}OC(O)NR^{10}-$, and
c) $C_1-C_6$ alkyl substituted by $C_1-C_6$ perfluoroalkyl, $R^{10}O-$, $R^{10}C(O)NR^{10}-$, $(R^{10})_2N-C(NR^{10})-$, $R^{10}C(O)-$, $R^{10}OC(O)-$, $-N(R^{10})_2$, or $R^{11}OC(O)NR^{10}-$;
$R^{6a}$ is selected from:
$C_{1-4}$ alkyl or $C_{3-6}$ cycloalkyl, unsubstituted or substituted with:
a) $C_{1-4}$ alkoxy,
b) halogen, or
c) aryl or heterocycle;
$R^8$ is independently selected from:
a) hydrogen,
b) $C_1-C_6$ alkyl, $C_2-C_6$ alkenyl, $C_2-C_6$ alkynyl, $C_1-C_6$ perfluoroalkyl, F, Cl, $R^{10}O-$, $R^{10}C(O)NR^{10}-$, CN, $NO_2$, $(R^{10})_2N-C(NR^{10})-$, $R^{10}C(O)-$, $-N(R^{10})_2$, or $R^{11}OC(O)NR^{10}-$, and
c) $C_1-C_6$ alkyl substituted by $C_1-C_6$ perfluoroalkyl, $R^{10}O-$, $R^{10}C(O)NR^{10}$, $(R^{10})_2N-C(NR^{10})-$, $R^{10}C(O)-$, $-N(R^{10})_2$, or $R^{11}OC(O)NR^{10}-$;
$R^{10}$ is independently selected from hydrogen, $C_1-C_6$ alkyl, benzyl and aryl;
$R^{11}$ is independently selected from $C_1-C_6$ alkyl and aryl;
X is $-CH_2-$ or $-C(=O)-$;
Y is a bond, $-CH_2-$, $-NH-$, $-S(=O)_m-$ or O;
Z is selected from:
1) a unsubstituted or substituted group selected from aryl, heteroaryl, arylmethyl, heteroarylmethyl, arylsulfonyl, heteroarylsulfonyl, wherein the substituted group is substituted with one or more of the following:
a) $C_{1-4}$ alkyl, unsubstituted or substituted with: $C_{1-4}$ alkoxy, $NR^6R^7$, $C_{3-6}$ cycloalkyl, aryl, heterocycle, HO, $-S(O)_mR^{6a}$, or $-C(O)NR^6R^7$,
b) aryl or heterocycle,
c) halogen,
d) $OR^6$,
e) $NR^6R^7$,
f) CN,
g) $NO_2$,
h) $CF_3$;
i) $-S(O)_mR^{6a}$,
j) $-C(O)NR^6R^7$, or
k) $C_3-C_6$ cycloalkyl; or
2) unsubstituted $C_1-C_6$ alkyl, substituted $C_1-C_6$ alkyl, unsubstituted $C_3-C_6$ cycloalkyl or substituted $C_3-C_6$ cycloalkyl, wherein the substituted $C_1-C_6$ alkyl and substituted $C_3-C_6$ cycloalkyl is substituted with one or two of the following:
a) $C_{1-4}$ alkoxy,
b) $NR^6R^7$,
c) $C_{3-6}$ cycloalkyl,
d) $-NR^6C(O)R^7$,
e) HO,
f) $-S(O)_mR^{6a}$,
g) halogen, or
h) perfluoroalkyl;
m is 0, 1 or 2; and
p is 0, 1, 2, 3 or 4;

or the pharmaceutically acceptable salts thereof.

In a second more preferred embodiment of this invention, the inhibitors of farnesyl-protein transferase are illustrated by the formula D:

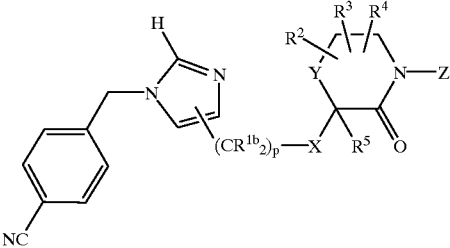

wherein:

R$^{1b}$ is independently selected from:
  a) hydrogen,
  b) aryl, heterocycle, cycloalkyl, R$^{10}$O—, —N(R$^{10}$)$_2$ or C$_2$–C$_6$ alkenyl,
  c) C$_1$–C$_6$ alkyl unsubstituted or substituted by aryl, heterocycle, cycloalkyl, alkenyl, R$^{10}$O—, or —N(R$^{10}$)$_2$;

R$^2$ and R$^4$ are independently selected from: hydrogen or C$_1$–C$_6$ alkyl;

R$^3$ and R$^5$ are hydrogen;

R$^6$ and R$^7$ are independently selected from:
  a) hydrogen,
  b) C$_1$–C$_6$ alkyl, C$_2$–C$_6$ alkenyl, C$_2$–C$_6$ alkynyl, C$_1$–C$_6$ perfluoroalkyl, F, Cl, R$^{10}$O—, R$^{10}$C(O)NR$^{10}$—, CN, NO$_2$, (R$^{10}$)$_2$N—C(NR$^{10}$)—, R$^{10}$C(O)—, R$^{10}$OC(O)—, —N(R$^{10}$)$_2$, or R$^{11}$OC(O)NR$^{10}$—, and
  c) C$_1$–C$_6$ alkyl substituted by C$_1$–C$_6$ perfluoroalkyl, R$^{10}$O—, R$^{10}$C(O)NR$^{10}$, (R$^{10}$)$_2$N—C(NR$^{10}$), R$^{10}$C(O)—, R$^{10}$OC(O)—, —N(R$^{10}$)$_2$, or R$^{11}$OC(O)NR$^{10}$—;

R$^{10}$ is independently selected from hydrogen, C$_1$–C$_6$ alkyl, benzyl and aryl;

R$^{11}$ is independently selected from C$_1$–C$_6$ alkyl and aryl;

X is —CH$_2$— or —C(=O)—;

Y is a bond, —CH$_2$—, —NH—, —S(=O)$_m$— or O;

Z is mono- or bicyclic aryl, mono- or bicyclic heteroaryl, mono- or bicyclic arylmethyl, mono- or bicyclic heteroarylmethyl, mono- or bicyclic arylsulfonyl, mono- or bicyclic heteroarylsulfonyl, unsubstituted or substituted with one or two of the following:
  1) C$_{1-4}$ alkyl, unsubstituted or substituted with:
    a) C$_{1-4}$ alkoxy,
    b) NR$^6$R$^7$,
    c) C$_{3-6}$ cycloalkyl,
    d) aryl or heterocycle,
    e) HO,
    f) —S(O)$_m$R$^6$, or
    g) —C(O)NR$^6$R$^7$,
  2) aryl or heterocycle,
  3) halogen,
  4) OR$^6$,
  5) NR$^6$R$^7$,
  6) CN,
  7) NO$_2$,
  8) CF$_3$;
  9) —S(O)$_m$R$^6$,
  10) —C(O)NR$^6$R$^7$, or
  11) C$_3$–C$_6$ cycloalkyl;
m is 0, 1 or 2; and
p is 0, 1, 2, 3 or 4;
or the pharmaceutically acceptable salts thereof.

The preferred compounds of this invention are as follows:
N-[2-{1-(4-Cyanobenzyl)-5-imidazolyl}ethyl]-3-carbamoyl-1-phenyl-2-piperidinone
3-[3-{1-(4-Cyanobenzyl)-5-imidazolyl}-1-propyl]-1-phenyl-2-piperidinone
3-[3-{1-(4-Cyanobenzyl)-5-imidazolyl}-1-propyl]-1-phenyl-2-pyrrolidinone
(±)cis—3-[3-{1-(4-Cyanobenzyl)-5-imidazolyl}-1-propyl]-4-methoxymethyl-1-phenyl-2-pyrrolidinone
(±)trans-3-[3-{1-(4-Cyanobenzyl)-5-imidazolyl}-1-propyl]-4-methoxymethyl-1-phenyl-2-pyrrolidinone
3-[2-{5-(4-Cyanobenzyl)-1-imidazolyl}-1-ethyl]-1-phenyl-2-pyrrolidinone
1-Benzyl-3-[2-{5-(4-cyanobenzyl)-1-imidazolyl}-1-ethyl]-2-pyrrolidinone and
(±)-1-(3-chloropheny)-3-[1-(1-(4-cyanobenzyl)-5-imidazolyl)-1-(hydroxy)methyl]-2-piperazinone
or the pharmaceutically acceptable salts or optical isomers thereof.

Specific examples of the compounds of the invention are:
N-[2-{1-(4-Cyanobenzyl)-5-imidazolyl}ethyl]-3-carbamoyl-1-phenyl-2-piperidinone

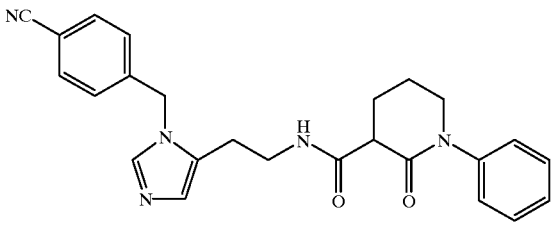

3-[2-{5-(4-Cyanobenzyl)-1-imidazolyl}-1-ethyl]-1-phenyl-2-pyrrolidinone

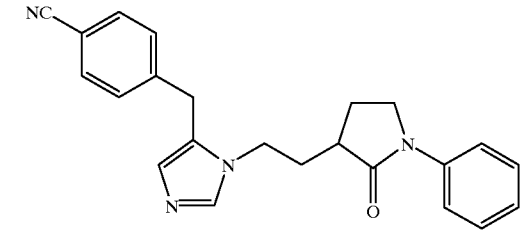

1-Benzyl-3-[2-{5-(4-cyanobenzyl)-1-imidazolyl}-1-ethyl]-2-pyrrolidinone

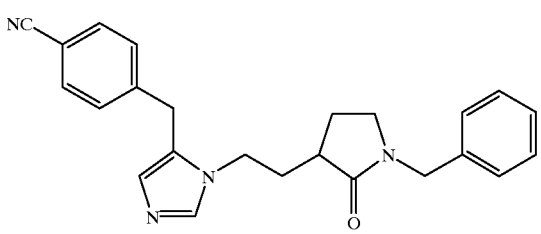

or the pharmaceutically acceptable salts thereof.

The compounds of the present invention may have asymmetric centers and occur as racemates, racemic mixtures, and as individual diastereomers, with all possible isomers, including optical isomers, being included in the present invention. When any variable (e.g. aryl, heterocycle, R$^1$, R$^2$ etc.) occurs more than one time in any constituent, its definition on each occurence is independent at every other occurence. Also, combinations of substituents/or variables are permissible only if such combinations result in stable compounds.

As used herein, "alkyl" is intended to include both branched and straight-chain saturated aliphatic hydrocarbon groups having the specified number of carbon atoms; "alkoxy" represents an alkyl group of indicated number of carbon atoms attached through an oxygen bridge. "Halogen" or "halo" as used herein means fluoro, chloro, bromo and iodo.

As used herein, "aryl" is intended to mean any stable monocyclic or bicyclic carbon ring of up to 7 members in each ring, wherein at least one ring is aromatic. Examples of such aryl elements include phenyl, naphthyl, tetrahydronaphthyl, indanyl, biphenyl, phenanthryl, anthryl or acenaphthyl.

The term heterocycle or heterocyclic, as used herein, represents a stable 5- to 7-membered monocyclic or stable 8- to 11-membered bicyclic heterocyclic ring which is either saturated or unsaturated, and which consists of carbon atoms and from one to four heteroatoms selected from the group consisting of N, O, and S, and including any bicyclic group in which any of the above-defined heterocyclic rings is fused to a benzene ring. The heterocyclic ring may be attached at any heteroatom or carbon atom which results in the creation of a stable structure. Examples of such heterocyclic elements include, but are not limited to, azepinyl, benzimidazolyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dihydrobenzothienyl, dihydrobenzothiopyranyl, dihydrobenzothiopyranyl sulfone, furyl, imidazolidinyl, imidazolinyl, imidazolyl, indolinyl, indolyl, isochromanyl, isoindolinyl, isoquinolinyl, isothiazolidinyl, isothiazolyl, isothiazolidinyl, morpholinyl, naphthyridinyl, oxadiazolyl, 2-oxoazepinyl, oxazolyl, 2-oxopiperazinyl, 2-oxopiperdinyl, 2-oxopyrrolidinyl, piperidyl, piperazinyl, pyridyl, pyrazinyl, pyrazolidinyl, pyrazolyl, pyridazinyl, pyrimidinyl, pyrrolidinyl, pyrrolyl, quinazolinyl, quinolinyl, quinoxalinyl, tetrahydrofuryl, tetrahydroisoquinolinyl, tetrahydroquinolinyl, thiamorpholinyl, thiamorpholinyl sulfoxide, thiazolyl, thiazolinyl, thienofuryl, thienothienyl, and thienyl.

As used herein, "heteroaryl" is intended to mean any stable monocyclic or bicyclic carbon ring of up to 7 members in each ring, wherein at least one ring is aromatic and wherein from one to four carbon atoms are replaced by heteroatoms selected from the group consisting of N, O, and S. Examples of such heterocyclic elements include, but are not limited to, benzimidazolyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dihydrobenzothienyl, dihydrobenzothiopyranyl, dihydrobenzothiopyranyl sulfone, furyl, imidazolyl, indolinyl, indolyl, isochromanyl, isoindolinyl, isoquinolinyl, isothiazolyl, naphthyridinyl, oxadiazolyl, pyridyl, pyrazinyl, pyrazolyl, pyridazinyl, pyrimidinyl, pyrrolyl, quinazolinyl, quinolinyl, quinoxalinyl, tetrahydroisoquinolinyl, tetrahydroquinolinyl, thiazolyl, thienofuryl, thienothienyl, and thienyl.

As used herein in the definition of $R^2$ and $R^4$, the term "the substituted group" intended to mean a substituted $C_{1-8}$ alkyl, substituted $C_{2-8}$ alkenyl, substituted $C_{2-8}$ alkynyl, substituted aryl or substituted heterocycle from which the substitutent(s) $R^2$ and $R^3$ are selected.

As used herein in the definition of $R^6$, $R^{6a}$, $R^7$ and $R^{7a}$, the substituted $C_{1-8}$ alkyl, substituted $C_{3-6}$ cycloalkyl, substituted aroyl, substituted aryl, substituted heteroaroyl, substituted arylsulfonyl, substituted heteroarylsulfonyl and substituted heterocycle include moieties containing from 1 to 3 substitutents in addition to the point of attachment to the rest of the compound. Preferably, such substitutents are selected from the group which includes but is not limited to F, Cl, Br, $CF_3$, $NH_2$, $N(C_1-C_6 \text{ alkyl})_2$, $NO_2$, CN, $(C_1-C_6 \text{ alkyl})O$—, —OH, $(C_1-C_6 \text{ alkyl})S(O)_m$—, $(C_1-C_6 \text{ alkyl})C(O)NH$—, $H_2N$—C(NH)—, $(C_1-C_6 \text{ alkyl})C(O)$—, $(C_1-C_6 \text{ alkyl})OC(O)$—, $N_3$,$(C_1-C_6 \text{ alkyl})OC(O)NH$—, phenyl, pyridyl, imidazolyl, oxazolyl, isoxazolyl, thiazolyl, thienyl, furyl, isothiazolyl and $C_1-C_{20}$ alkyl.

When $R^2$ and $R^3$ are combined to form —$(CH_2)_u$—, cyclic moieties are formed. Examples of such cyclic moieties include, but are not limited to:

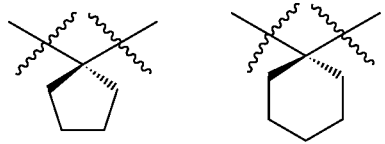

In addition, such cyclic moieties may optionally include a heteroatom(s). Examples of such heteroatom-containing cyclic moieties include, but are not limited to:

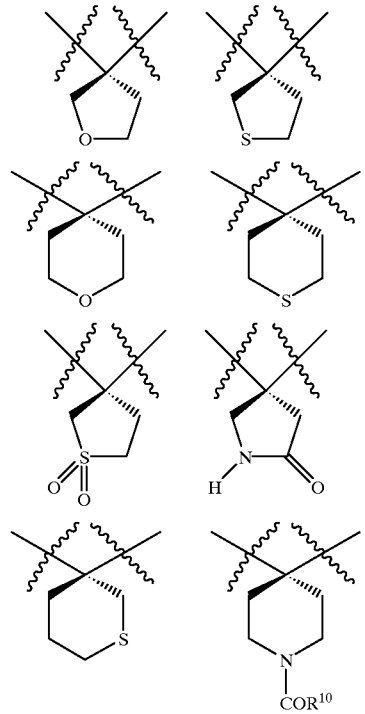

Lines drawn into the ring systems from substituents (such as from $R^2$, $R^3$, $R^4$ etc.) indicate that the indicated bond may be attached to any of the substitutable ring carbon atoms.

Preferably, $R^{1a}$ and $R^{1b}$ are independently selected from: hydrogen, —$N(R^{10})_2$, $R^{10}C(O)NR^{10}$— or unsubstituted or substituted $C_1$–$C_6$ alkyl wherein the substituent on the substituted $C_1$–$C_6$ alkyl is selected from unsubstituted or substituted phenyl, —$N(R^{10})_2$, $R^{10}O$— and $R^{10}C(O)NR^{10}$—.

Preferably, $R^2$ is selected from: H,

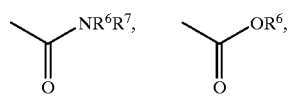

and an unsubstituted or substituted group, the group selected from $C_{1-8}$ alkyl, $C_{2-8}$ alkenyl and $C_{2-8}$ alkynyl;
wherein the substituted group is substituted with one or more of:
1) aryl or heterocycle, unsubstituted or substituted with:
   a) $C_{1-4}$ alkyl,
   b) $(CH_2)_pOR^6$,
   c) $(CH_2)_pNR^6R^7$,
   d) halogen,
2) $C_{3-6}$ cycloalkyl,
3) $OR^6$,
4) $SR^{6a}$, $S(O)R^{6a}$, $SO_2R^{6a}$,
5) —$NR^6R^7$

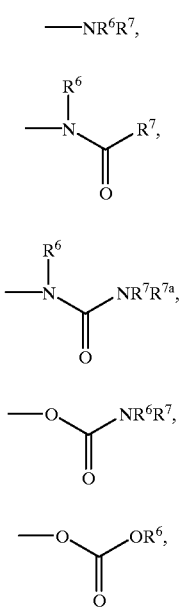

15) $N_3$, or
16) F.

Preferably, $R^3$ is selected from: hydrogen and $C_1$–$C_6$ alkyl.

Preferably, $R^4$ and $R^5$ are hydrogen.

Preferably, $R^6$, $R^7$ and $R^{7a}$ is selected from: hydrogen, unsubstituted or substituted $C_1$–$C_6$ alkyl, unsubstituted or substituted aryl and unsubstituted or substituted cycloalkyl.

Preferably, $R^{6a}$ is unsubstituted or substituted $C_1$–$C_6$ alkyl, unsubstituted or substituted aryl and unsubstituted or substituted cycloalkyl.

Preferably, $R^9$ is hydrogen or methyl. Most preferably, $R^a$ is hydrogen.

Preferably, $R^{10}$ is selected from H, $C_1$–$C_6$ alkyl and benzyl.

Preferably, $A^1$ and $A^2$ are independently selected from: a bond, —$C(O)NR^{10}$—, —$NR^{10}C(O)$—, O, —$N(R^{10})$—, —$S(O)_2N(R^{10})$— and —$N(R^{10})S(O)_2$—.

Preferably, V is selected from hydrogen, heterocycle and aryl. More preferably, V is phenyl.

Preferably, Y is a bond or —$CH_2$—. More preferably, Y is —$CH_2$—.

Preferably, Z is selected from unsubstituted or substituted phenyl, unsubstituted or substituted naphthyl, unsubstituted or substituted pyridyl, unsubstituted or substituted furanyl and unsubstituted or substituted thienyl. More preferably, Z is unsubstituted or substituted phenyl.

Preferably, W is selected from imidazolinyl, imidazolyl, oxazolyl, pyrazolyl, pyyrolidinyl, thiazolyl and pyridyl. More preferably, W is selected from imidazolyl and pyridyl.

Preferably, n and r are independently 0, 1, or 2.
Preferably p is 1, 2 or 3.
Preferably s is 0.
Preferably t is 1.
Preferably, the moiety

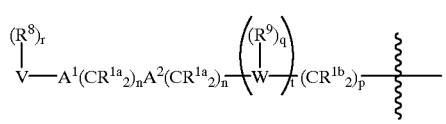

is selected from:

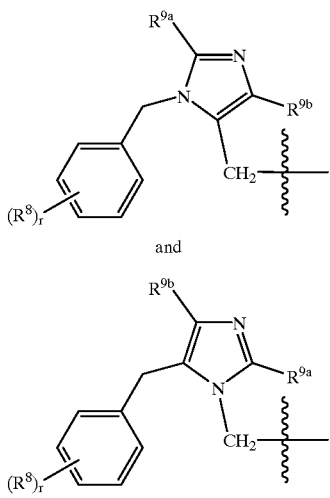

and

It is intended that the definition of any substituent or variable (e.g., $R^{1a}$, $R^9$, n, etc.) at a particular location in a molecule be independent of its definitions elsewhere in that molecule. Thus, —N($R^{10}$)$_2$ represents —NHH, —NHCH$_3$, —NHC$_2$H$_5$, etc. It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials.

The pharmaceutically acceptable salts of the compounds of this invention include the conventional non-toxic salts of the compounds of this invention as formed, e.g., from non-toxic inorganic or organic acids. For example, such conventional non-toxic salts include those derived from inorganic acids such as hydrochloric, hydrobromic, sulfuric, sulfamic, phosphoric, nitric and the like: and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxy-benzoic, fumaric, toluenesulfonic, methanesulfonic, ethane disulfonic, oxalic, isethionic, trifluoroacetic and the like.

The pharmaceutically acceptable salts of the compounds of this invention can be synthesized from the compounds of this invention which contain a basic moiety by conventional chemical methods. Generally, the salts are prepared either by ion exchange chromatography or by reacting the free base with stoichiometric amounts or with an excess of the desired salt-forming inorganic or organic acid in a suitable solvent or various combinations of solvents.

Reactions used to generate the compounds of this invention are prepared by employing reactions as shown in the Schemes 1–15, in addition to other standard manipulations such as ester hydrolysis, cleavage of protecting groups, etc., as may be known in the literature or exemplified in the experimental procedures. Substituent R, as shown in the Schemes, represents the substituents $R^2$, $R^3$, $R^4$, and $R^5$; however the point of attachment to the ring is illustrative only and is not meant to be limiting.

These reactions may be employed in a linear sequence to provide the compounds of the invention or they may be used to synthesize fragments which are subsequently joined by the reductive alkylation reactions described in the Schemes. Synopsis of Schemes 1–15:

The requisite intermediates are in some cases commercially available, or can be prepared according to literature procedures, for the most part. In Scheme 1, for example, the synthesis of 3-substituted-2-piperidone is outlined. Thus a suitably substituted 2-hydroxynicotinic acid I may be catalytically hydrogenated to provide the 2-piperidone II. This intermediate may be coupled to a suitably substituted aryl moiety to provide the key intermediate III. The ester of compound III can be saponified and the acid can be reacted with an amine such as IV to provide the instant compound V.

Alternatively, as shown in Scheme 2, intermediate III can be deprotonated and reacted with an electrophile, such as VI, to provide the instant compound VII. Compound VII can also be decarboxylated to provide the instant compound VIII. Similar coupling to an aryl moiety, deprotonation and alkylation can be performed on a pyrrolidinone, as shown in Scheme 3, to provide the instant compound IX.

Scheme 3a illustrates an alternative synthesis of the pyrrolidinone compounds of the instant invention. Thus a suitably substituted 4-halobutanoyl chloride may be cyclized with an amine in a two step procedure and then selectively functionalized adjacent to the carbonyl to provide the instant compound having a preferred arylmethylimidazolyl moiety.

Preparation of the instant compounds wherein Y is NH is illustrated in Schem 3b. Thus the suitably substituted N-aminoethylaniline is prepared and undergoes a two step cyclization with chloroacetyl chloride to provide the protected piperazinone. This intermediate can undergo selective alkylation reactions such as illustrated in Scheme 3 and hereinbelow. After incorporation of a moiety at the 3-position, the N-protecting group may be removed by methods known in the art, such as with HCl in ethyl acetate.

Scheme 3c illustrates preparation of the instant compounds wherein Y is S. The suitably substituted thiomorpholinone may be selectively alkylated with reagents illustrated in Scheme 3 and hereinbelow and may also be oxidized subsequent to the alkylation as shown in the scheme. Preparation of a thiomorpholinone intermediate having a substituent in the 5-position is illustrated in Scheme 3d.

Scheme 4 illustrates preparation of the instant copounds wherein the linker X is an amine. As shown in the Scheme the amine intermediate X may be alkylated with a suitably substituted electrophile.

The amine intermediate X can be reductively alkylated with a variety of aldehydes, such as XI. The aldehydes can be prepared by standard procedures, such as that described by O. P. Goel, U. Krolls, M. Stier and S. Kesten in *Organic Syntheses*, 1988, 67, 69–75, from the appropriate amino acid (Scheme 3). The reductive alkylation can be accomplished at pH 5–7 with a variety of reducing agents, such as sodium triacetoxyborohydride or sodium cyanoborohydride in a solvent such as dichloroethane, methanol or dimethylformamide. The product XII can be deprotected to give the final compounds XIII with trifluoroacetic acid in methylene chloride. The final product XIII is isolated in the salt form, for example, as a trifluoroacetate, hydrochloride or acetate salt, among others. The product diamine XIII can further be selectively protected to obtain XIV, which can subsequently be reductively alkylated with a second aldehyde to obtain XV. Removal of the protecting group, and conversion to cyclized products such as the dihydroimidazole XVI can be accomplished by literature procedures.

Alternatively, the piperidone intermediate X can be reductively alkylated with other aldehydes such as 1-trityl-4-imidazolylcarboxaldehyde or 1-trityl-4-imidazolylacetaldehyde, to give products such as XVII (Scheme 6). The trityl protecting group can be removed from XVII to give XVIII, or alternatively, XVII can first be treated with an alkyl halide then subsequently deprotected to give the alkylated imidazole XIX. Alternatively, the intermediate X can be acylated or sulfonylated by standard techniques. The imidazole acetic acid XX can be converted to the acetate XXI by standard procedures, as shown in Scheme 7, and XXI can be first reacted with an alkyl halide, then treated with refluxing methanol to provide the regiospecifically alkylated imidazole acetic acid ester XXII. Hydrolysis and reaction with intermediate X in the presence of condensing reagents such as 1-(3-dimethylaminopropyl)-3-ethylcarbodiimide (EDC) leads to acylated products such as XXIV.

Scheme 7a illustrates the preparation of a suitably substituted benzylimidazolyl aldehyde intermediate whch may be reacted with the piperazinone and thiomorpholinone intermediates whose syntheses is described in Schemes 3b–3d (Scheme 7a and 7b).

If the intermediate X is reductively alkylated with an aldehyde which also has a protected hydroxyl group, such as XXV in Scheme 9, the protecting groups can be subsequently removed to unmask the hydroxyl group (Schemes 8, 9). The alcohol can be oxidized under standard conditions to e.g. an aldehyde, which can then be reacted with a, variety of organometallic reagents such as Grignard reagents, to obtain secondary alcohols such as XXIX. In addition, the fully deprotected amino alcohol XXX can be reductively alkylated (under conditions described previously) with a variety of aldehydes to obtain secondary amines, such as XXXI (Scheme 9), or tertiary amines.

The Boc protected amino alcohol XXVII can also be utilized to synthesize 2-aziridinylmethylpiperazines such as XXXII (Scheme 10). Treating XXVII with 1,1'-sulfonyldiimidazole and sodium hydride in a solvent such as dimethylformamide led to the formation of aziridine XXXII. The aziridine reacted in the presence of a nucleophile, such as a thiol, in the presence of base to yield the ring-opened product XXXIII.

In addition, the intermediate X can be reacted with aldehydes derived from amino acids such as O-alkylated tyrosines, according to standard procedures, to obtain compounds such as XXXIX, as shown in Scheme 11. When R' is an aryl group, XXXIX can first be hydrogenated to unmask the phenol, and the amine group deprotected with acid to produce XL. Alternatively, the amine protecting group in XXXIX can be removed, and O-alkylated phenolic amines such as XLI produced.

Schemes 12–15 illustrate syntheses of suitably substituted aldehydes useful in the syntheses of the instant compounds wherein the variable W is present as a pyridyl moiety. Similar synthetic strategies for preparing alkanols that incorporate other heterocyclic moieties for variable W are also well known in the art.

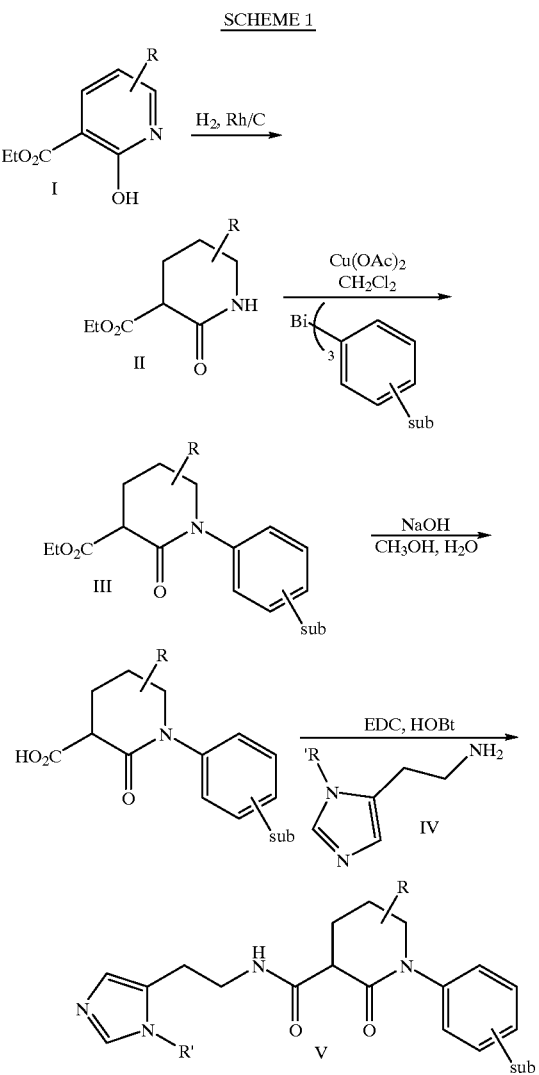

SCHEME 1

SCHEME 2
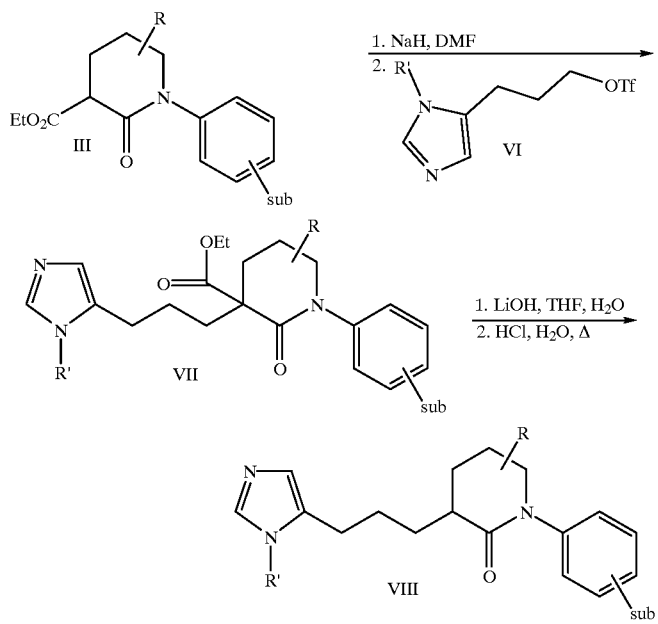
SCHEME 3
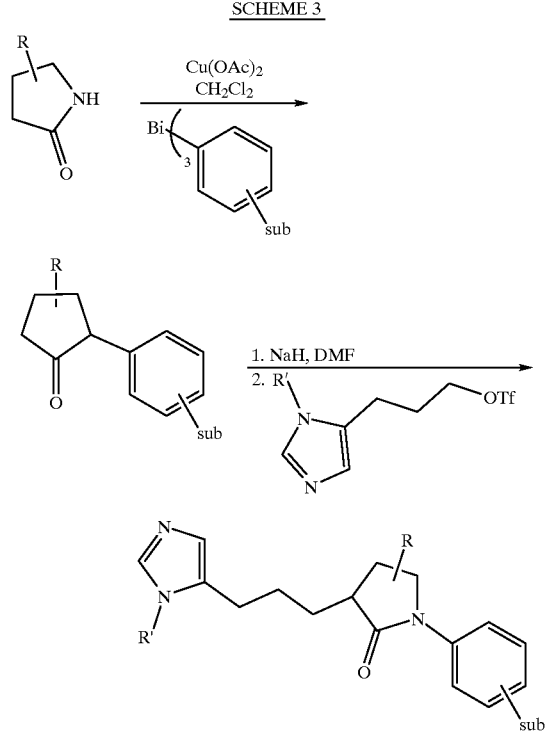
-continued
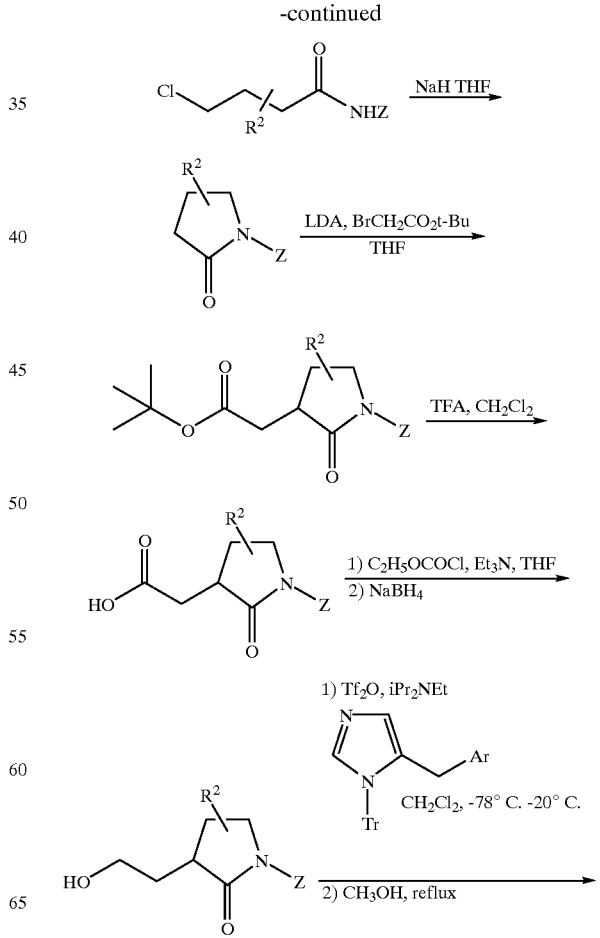
SCHEME 3a
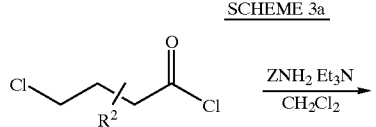

6,001,835
25
-continued
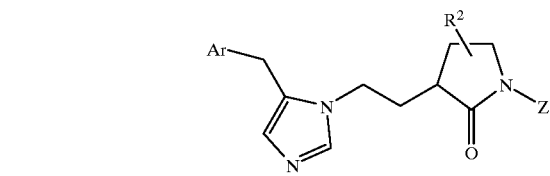
SCHEME 3b
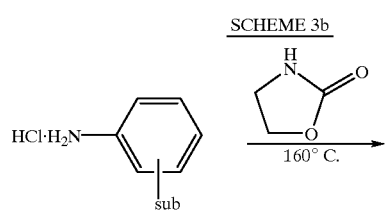
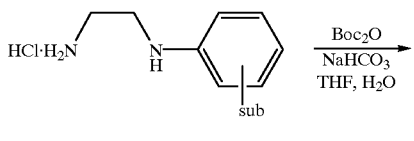
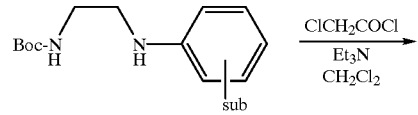
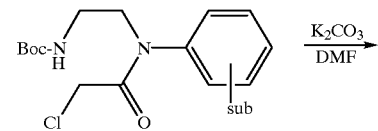
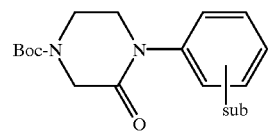
SCHEME 3c
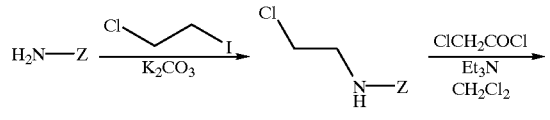
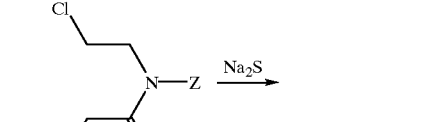
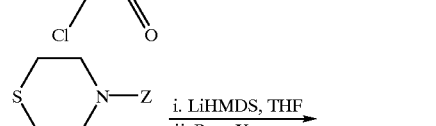
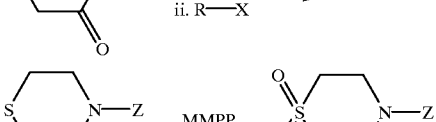
26
SCHEME 3d
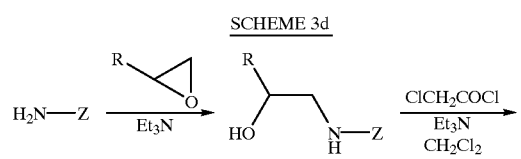
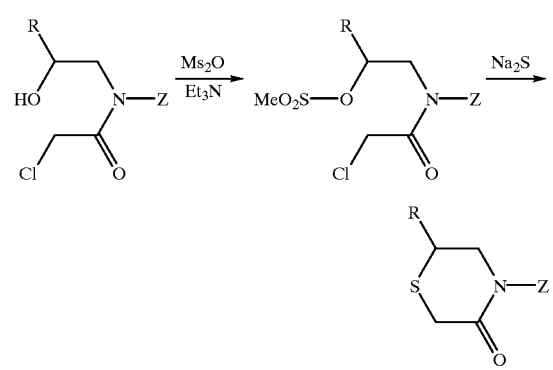
SCHEME 4
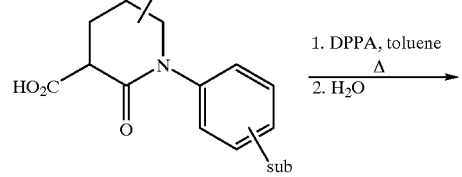
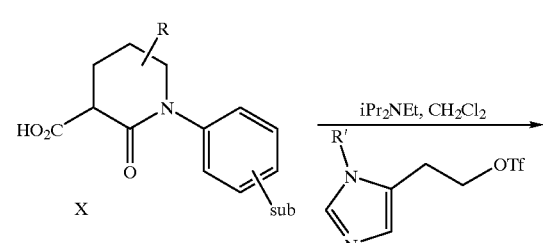
SCHEME 5
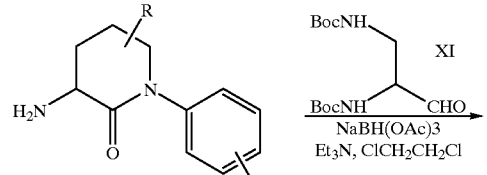

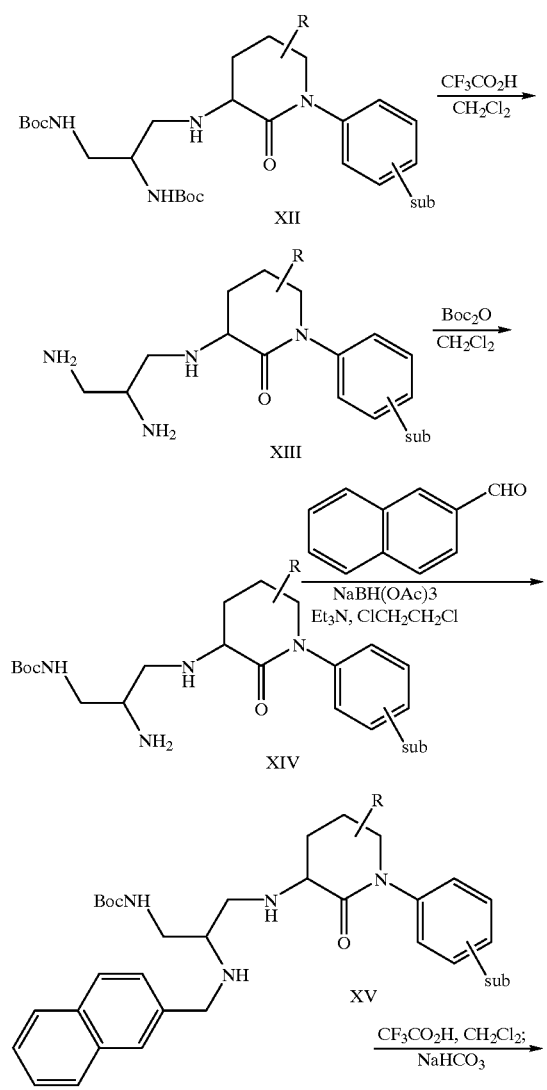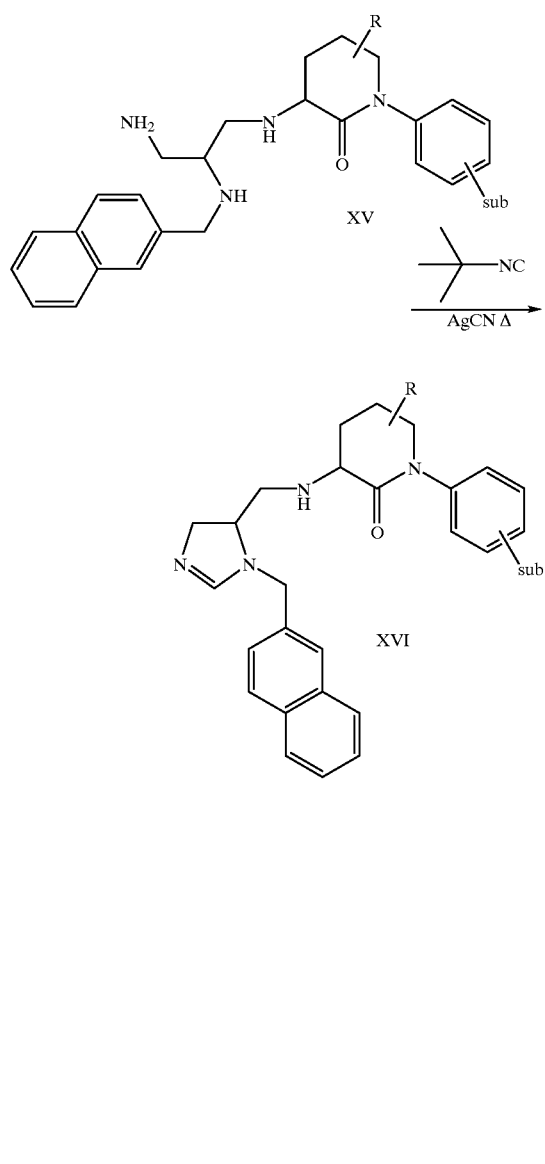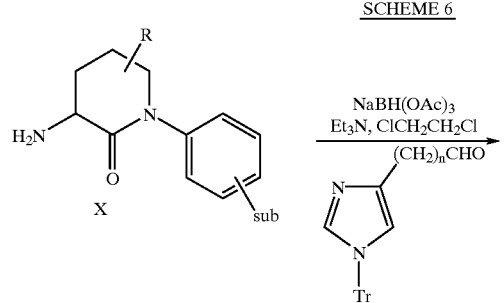

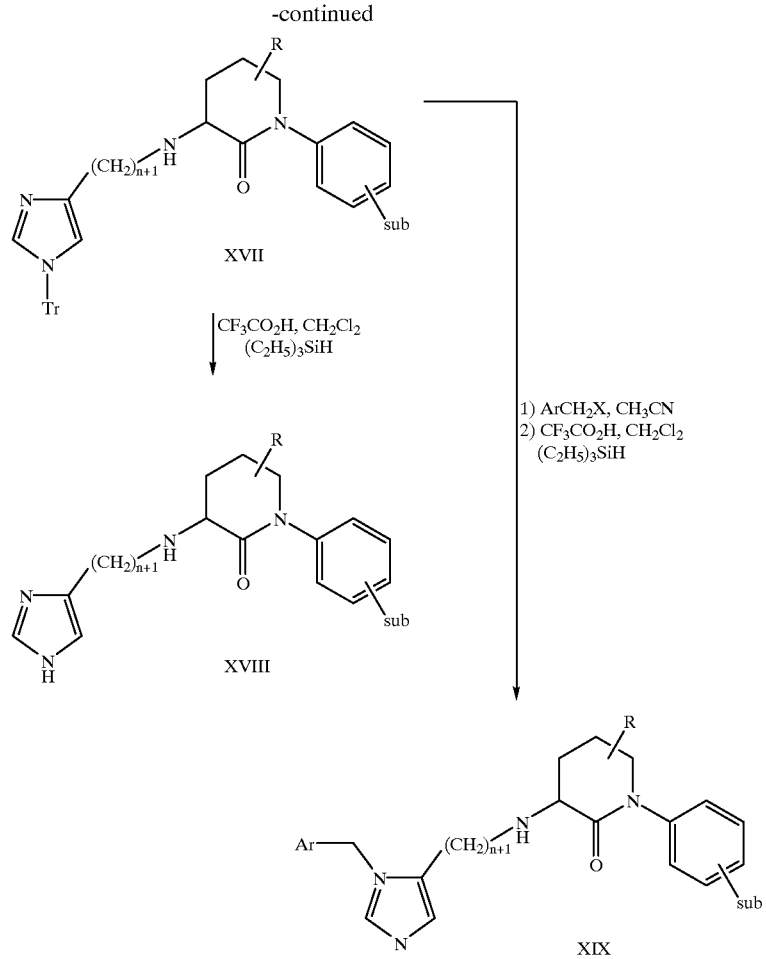

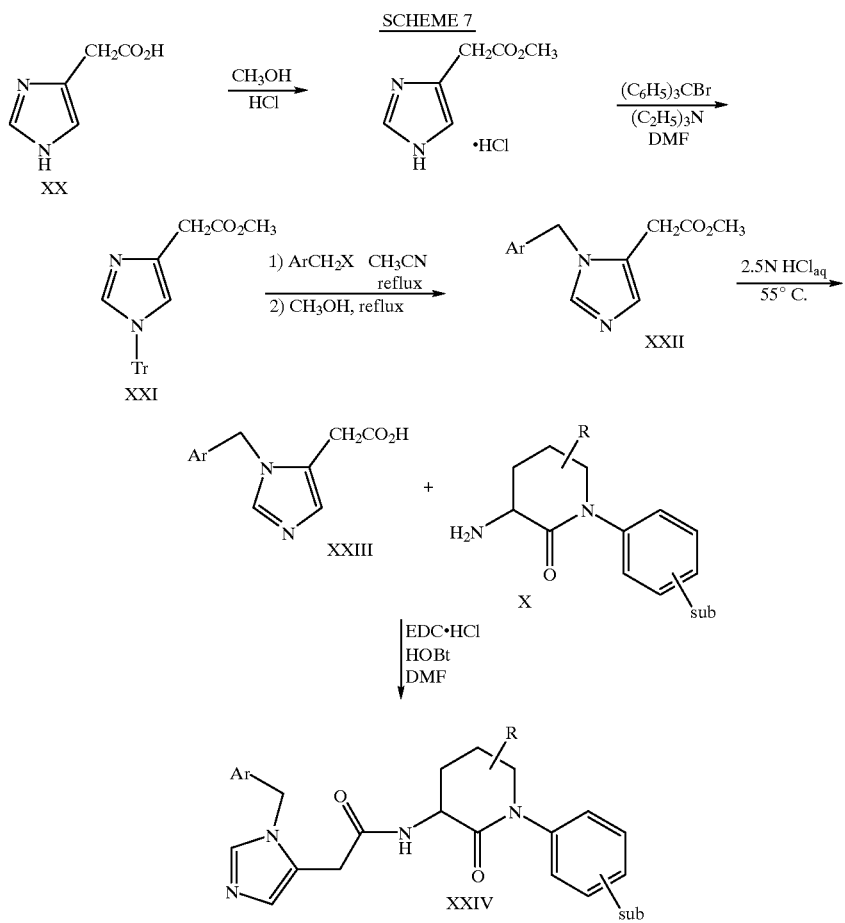
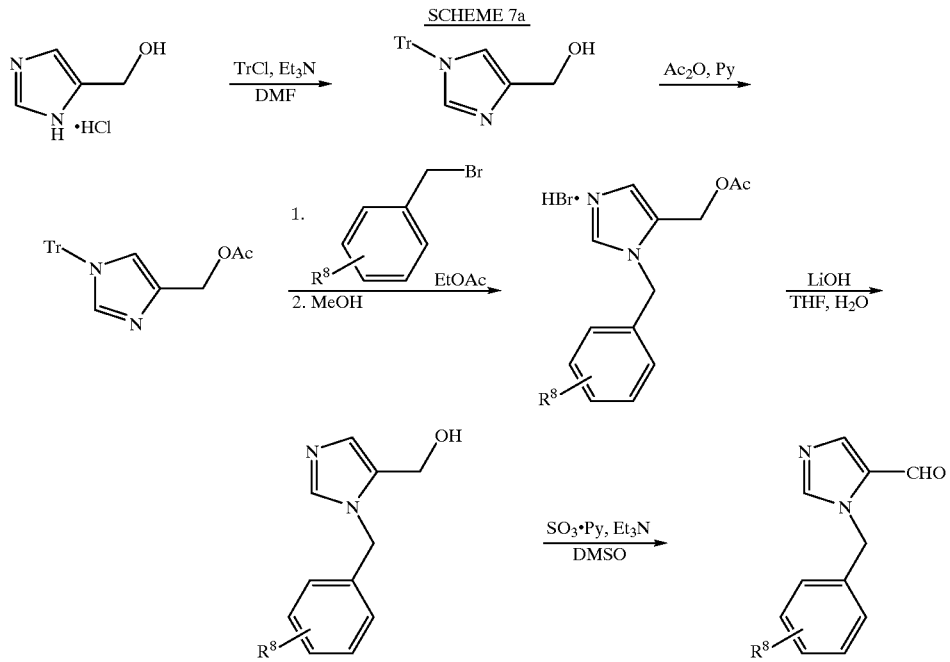

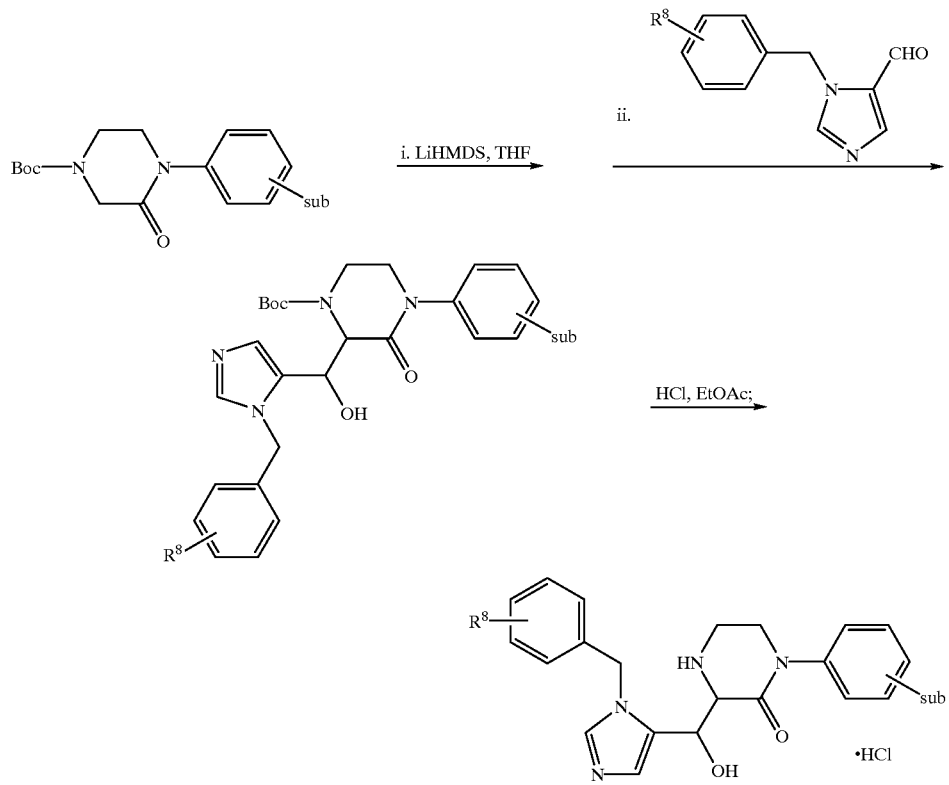
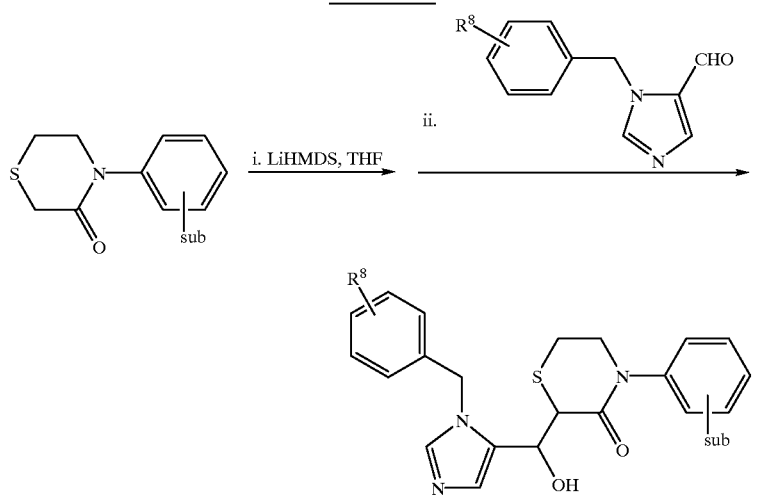

SCHEME 8
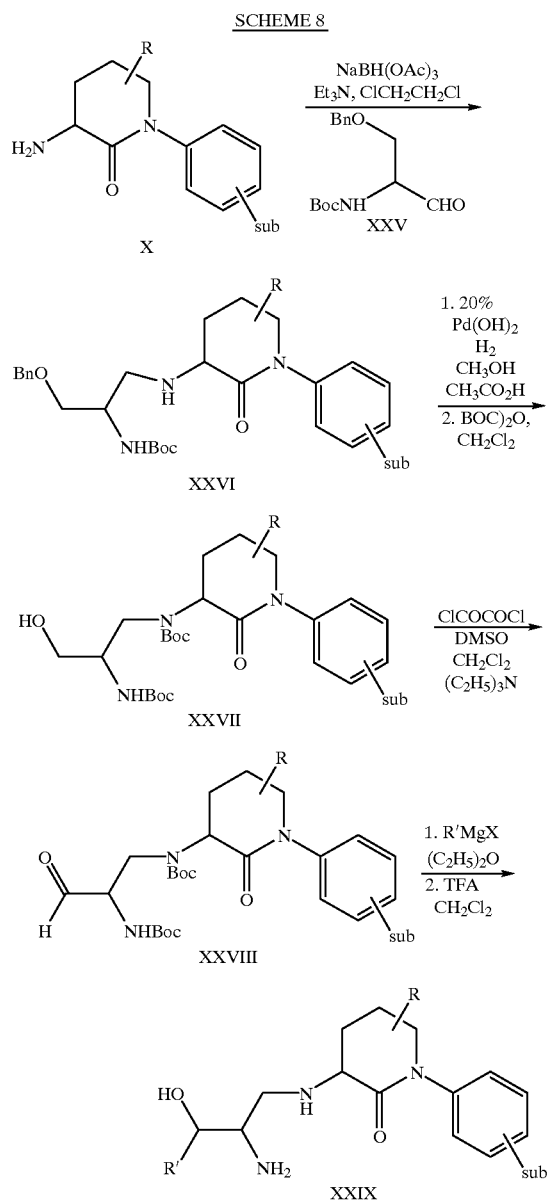
SCHEME 9
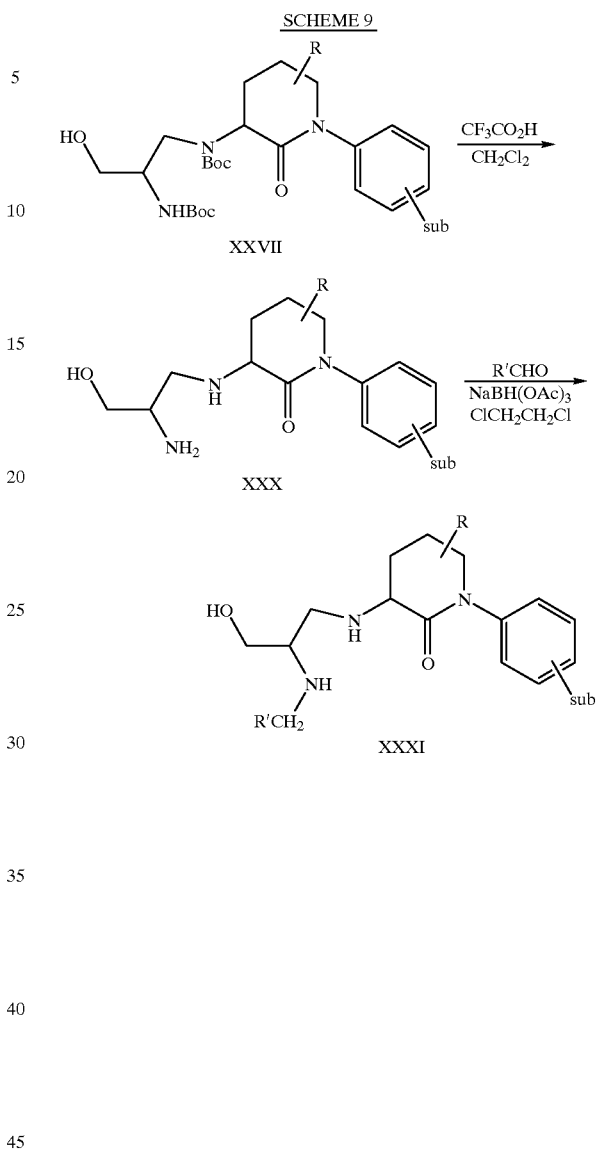
SCHEME 10
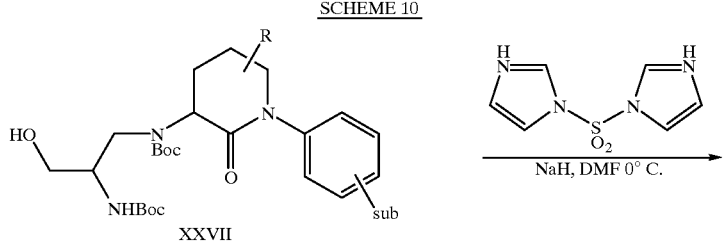

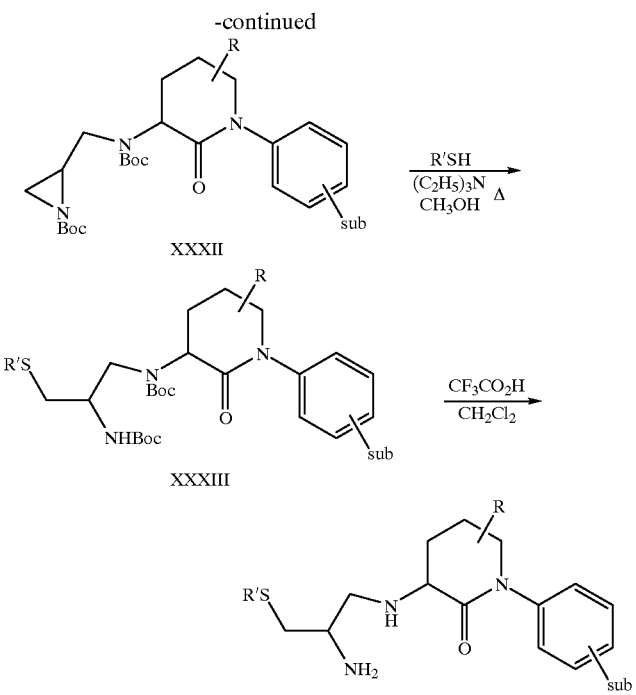
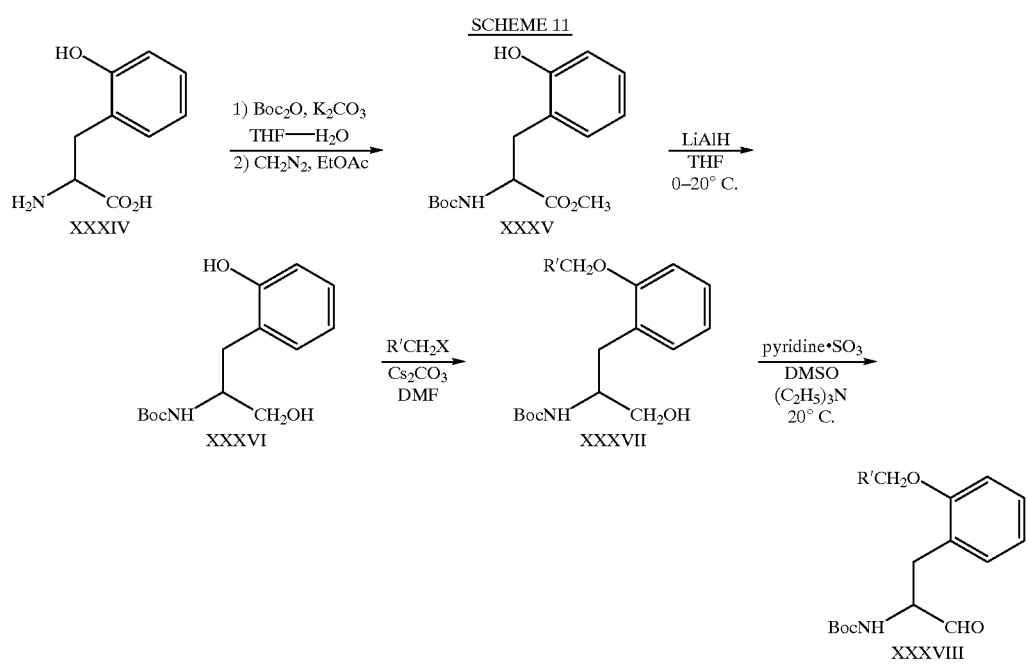

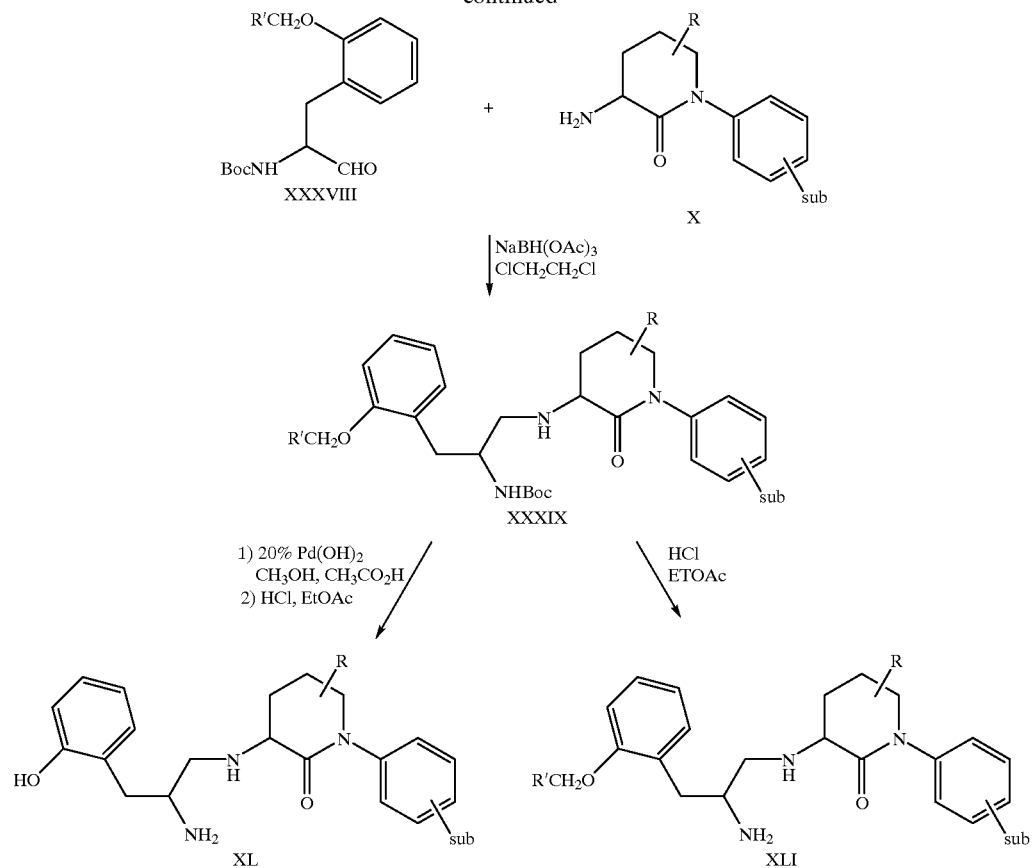
SCHEME 12
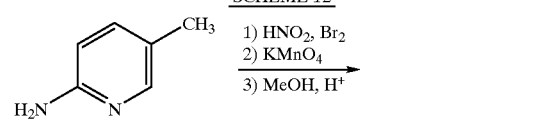
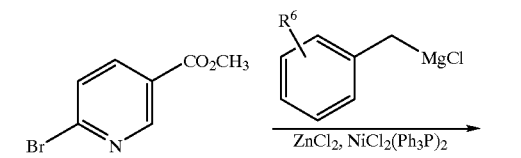
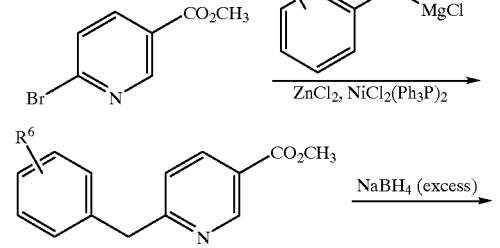
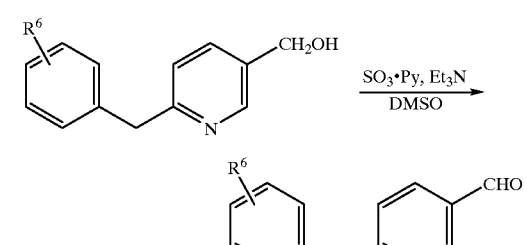
SCHEME 13
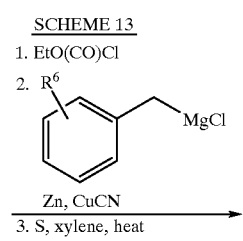
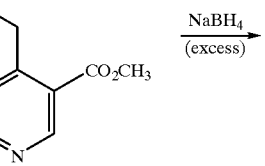

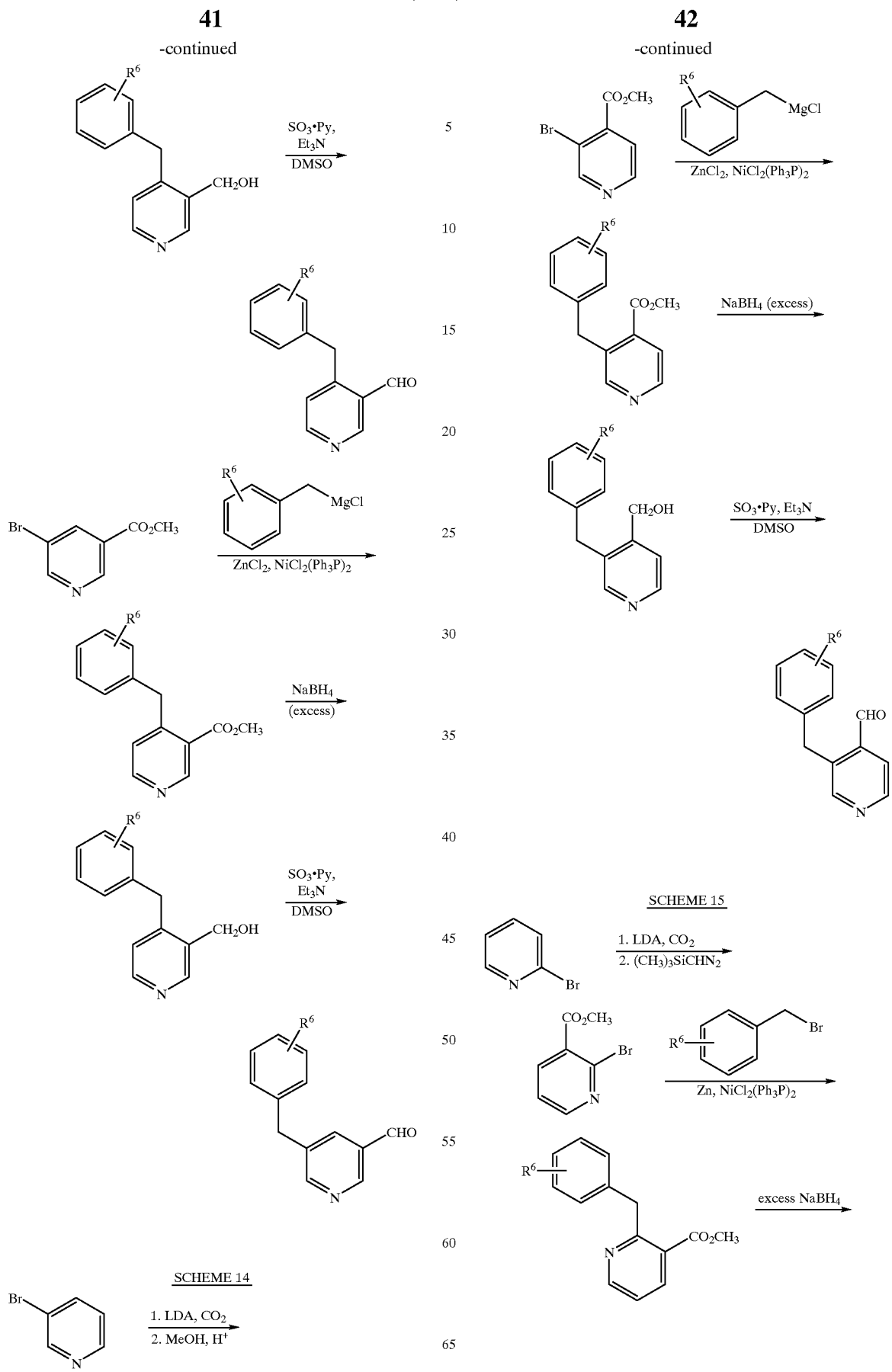

-continued

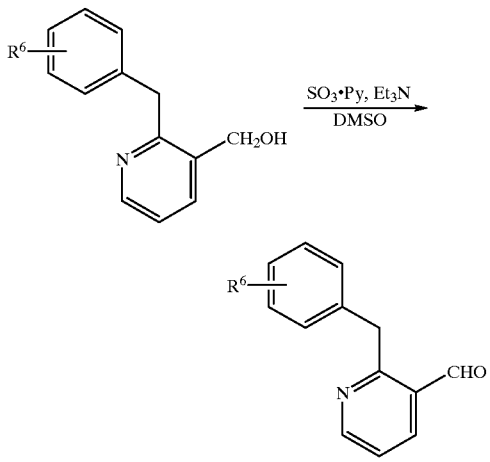

The instant compounds are useful as pharmaceutical agents for mammals, especially for humans. These compounds may be administered to patients for use in the treatment of cancer. Examples of the type of cancer which may be treated with the compounds of this invention include, but are not limited to, colorectal carcinoma, exocrine pancreatic carcinoma, myeloid leukemias and neurological tumors. Such tumors may arise by mutations in the ras genes themselves, mutations in the proteins that can regulate Ras activity (i.e., neurofibromin (NF-1), neu, scr, abl, lck, fyn) or by other mechanisms.

The compounds of the instant invention inhibit farnesyl-protein transferase and the farnesylation of the oncogene protein Ras. The instant compounds may also inhibit tumor angiogenesis, thereby affecting the growth of tumors (J. Rak et al. *Cancer Research,* 55:4575–4580 (1995)). Such anti-angiogenesis properties of the instant compounds may also be useful in the treatment of certain forms of blindness related to retinal vascularization.

The compounds of this invention are also useful for inhibiting other proliferative diseases, both benign and malignant, wherein Ras proteins are aberrantly activated as a result of oncogenic mutation in other genes (i.e., the Ras gene itself is not activated by mutation to an oncogenic form) with said inhibition being accomplished by the administration of an effective amount of the compounds of the invention to a mammal in need of such treatment. For example, a component of NF-1 is a benign proliferative disorder.

The instant compounds may also be useful in the treatment of certain viral infections, in particular in the treatment of hepatitis delta and related viruses (J. S. Glenn et al. *Science,* 256:1331–1333 (1992).

The compounds of the instant invention are also useful in the prevention of restenosis after percutaneous transluminal coronary angioplasty by inhibiting neointimal formation (C. Indolfi et al. *Nature medicine,* 1:541–545(1995).

The instant compounds may also be useful in the treatment and prevention of polycystic kidney disease (D. L. Schaffner et al. *American Journal of Pathology,* 142:1051–1060 (1993) and B. Cowley, Jr. et al. *FASEB Journal,* 2:A3160 (1989)).

The instant compounds may also be useful for the treatment of fungal infections.

The compounds of this invention may be administered to mammals, preferably humans, either alone or, preferably, in combination with pharmaceutically acceptable carriers or diluents, optionally with known adjuvants, such as alum, in a pharmaceutical composition, according to standard pharmaceutical practice. The compounds can be administered orally or parenterally, including the intravenous, intramuscular, intraperitoneal, subcutaneous, rectal and topical routes of administration.

For oral use of a chemotherapeutic compound according to this invention, the selected compound may be administered, for example, in the form of tablets or capsules, or as an aqueous solution or suspension. In the case of tablets for oral use, carriers which are commonly used include lactose and corn starch, and lubricating agents, such as magnesium stearate, are commonly added. For oral administration in capsule form, useful diluents include lactose and dried corn starch. When aqueous suspensions are required for oral use, the active ingredient is combined with emulsifying and suspending agents. If desired, certain sweetening and/or flavoring agents may be added. For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled in order to render the preparation isotonic.

The compounds of the instant invention may also be co-administered with other well known therapeutic agents that are selected for their particular usefulness against the condition that is being treated. For example, the instant compounds may be useful in combination with known anti-cancer and cytotoxic agents. Similarly, the instant compounds may be useful in combination with agents that are effective in the treatment and prevention of NF-1, restinosis, polycystic kidney disease, infections of hepatitis delta and related viruses and fungal infections.

If formulated as a fixed dose, such combination products employ the compounds of this invention within the dosage range described below and the other pharmaceutically active agent(s) within its approved dosage range. Compounds of the instant invention may alternatively be used sequentially with known pharmaceutically acceptable agent(s) when a combination formulation is inappropriate.

The present invention also encompasses a pharmaceutical composition useful in the treatment of cancer, comprising the administration of a therapeutically effective amount of the compounds of this invention, with or without pharmaceutically acceptable carriers or diluents. Suitable compositions of this invention include aqueous solutions comprising compounds of this invention and pharmacologically acceptable carriers, e.g., saline, at a pH level, e.g., 7.4. The solutions may be introduced into a patient's blood-stream by local bolus injection.

As used herein, the term "composition" is intended to encompass a product comprising the specified ingredients in the specific amounts, as well is any product which results, directly or indirectly, from combination of the specific ingredients in the specified amounts.

When a compound according to this invention is administered into a human subject, the daily dosage will normally be determined by the prescribing physician with the dosage generally varying according to the age, weight, and response of the individual patient, as well as the severity of the patient's symptoms.

In one exemplary application, a suitable amount of compound is administered to a mammal undergoing treatment for cancer. Administration occurs in an amount between about 0.1 mg/kg of body weight to about 60 mg/kg of body weight per day, preferably of between 0.5 mg/kg of body weight to about 40 mg/kg of body weight per day.

The compounds of the instant invention are also useful as a component in an assay to rapidly determine the presence and quantity of farnesyl-protein transferase (FPTase) in a composition. Thus the composition to be tested may be divided and the two portions contacted with mixtures which comprise a known substrate of FPTase (for example a tetrapeptide having a cysteine at the amine terminus) and farnesyl pyrophosphate and, in one of the mixtures, a compound of the instant invention. After the assay mixtures are incubated for an sufficient period of time, well known in the art, to allow the FPTase to farnesylate the substrate, the chemical content of the assay mixtures may be determined by well known immunological, radiochemical or chromatographic techniques. Because the compounds of the instant invention are selective inhibitors of FPTase, absence or quantitative reduction of the amount of substrate in the assay mixture without the compound of the instant invention relative to the presence of the unchanged substrate in the assay containing the instant compound is indicative of the presence of FPTase in the composition to be tested.

It would be readily apparent to one of ordinary skill in the art that such an assay as described above would be useful in identifying tissue samples which contain farnesyl-protein transferase and quantitating the enzyme. Thus, potent inhibitor compounds of the instant invention may be used in an active site titration assay to determine the quantity of enzyme in the sample. A series of samples composed of aliquots of a tissue extract containing an unknown amount of farnesyl-protein transferase, an excess amount of a known substrate of FPTase (for example a tetrapeptide having a cysteine at the amine terminus) and farnesyl pyrophosphate are incubated for an appropriate period of time in the presence of varying concentrations of a compound of the instant invention. The concentration of a sufficiently potent inhibitor (i.e., one that has a Ki substantially smaller than the concentration of enzyme in the assay vessel) required to inhibit the enzymatic activity of the sample by 50% is approximately equal to half of the concentration of the enzyme in that particular sample.

EXAMPLES

Examples provided are intended to assist in a further understanding of the invention. Particular materials employed, species and conditions are intended to be further illustrative of the invention and not limitative of the reasonable scope thereof.

Example 1

N-[2-{1-(4-Cyanobenzyl)-5-imidazolyl}ethyl]-3-carbamoyl-1-phenyl-2-piperidinone hydrochloride

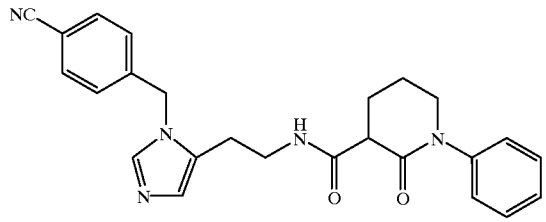

Step A: 4-Cyanobenzyl-N$^\alpha$-phthaloylhistamine

N$^\tau$-Pivaloyloxymethyl-N$^\alpha$-phthaloylhistamine (4.55 g, 12.8 mmol) was prepared as previously described (J. C. Emmett, F. H. Holloway, and J. L. Turner, *J. Chem. Soc., Perkin Trans.* 1, 1341, (1979)). α-Bromo-p-tolunitrile (3.77 g, 19.2 mmol) was dissolved in acetonitrile (70 mL). The solution was heated at 55° C. for 4 h, cooled to room temperature, and filtered to remove the white solid. The acetonitrile (30 mL) was concentrated to ½ its volume under reduced pressure and the solution was heated at 55° C. overnight. The solution was cooled and filtered to give a white solid. The volume of the filtrate was reduced to 10 mL, the solution was heated at 55° C. for 1 hr, then cooled to room temperature, diluted with EtOAc (25 mL) and filtered to obtain additional white solid. The solids were combined, dried, and dissolved in methanol (100 mL) which was saturated with ammonia gas while the temperature was maintained below 30° C. The solution was stirred for 1 hr, concentrated to dryness, and extracted with CH$_2$Cl$_2$ (3×200 mL), dried (MgSO$_4$), concentrated, and chromatographed (silica gel, 10:90:1 MeOH/CH$_2$Cl$_2$/NH$_4$OH) to give the title compound Step B: 4-Cyanobenzyl histamine 4-Cyanobenzyl-N$^\alpha$-phthaloylhistamine (1.64 g, 4.61 mmol), and hydrazine (1.46 mL, 46.1 mmol) were dissolved in absolute ethanol (70 mL). The solution was concentrated after 1 hr and filtered to remove a white precipitate which was washed several times with ethanol. The filtrate was concentrated and the residue was chromatographed (silica gel, 10:90:1 MeOH/CH$_2$Cl$_2$/NH$_4$OH) to give the title compound.

Step C: 3-Carbethoxy-1-phenyl-2-piperidinone

A mixture of 3-carbethoxy-2-piperidinone (1.00 g, 5.84 mmol), triphenylbismuth (3.95 g, 8.77 mmol), copper(II) acetate (1.58 g, 9.77 mmol) and triethylamine (1.22 mL, 8.77 mmol) was stirred for 17 h at 20° C. in dichloromethane (25 mL). The reaction mixture was adsorbed onto silica gel and eluted with 30–50% ethyl acetate/hexane. The title compund was obtained as an oil.

Step D: 3-Carboxy-1-phenyl-2-piperidinone

The product from Step C (0.551 g, 2.56 mmol) was dissolved in methanol (3 mL) and 5% aqueous sodium hydroxide added (3 mL). After 11 h, methanol was removed in vacuo, and the residue partitioned between ethyl acetate and 10% aqueous HCl. The organic layer was washed with saturated brine, and dried over $MgSO_4$. The title compound was obtained as a white solid.

Step E: N-[2-{1-(4-Cyanobenzyl)-5-imidazolyl}ethyl]-3-carbamoyl-1-phenyl-2-piperidinone hydrochloride The product from Step D (0.223 g, 1.01 mmol) was dissolved in dimethylformamide (5 mL). To this solution was added 4-cyanobenzyl histamine dihydrochloride (0.220 g, 0.184 mmol), EDC•HCl(0.191 g, 1.00 mmol) and 1-hydroxybenzotriazole (0.135 g, 1.00 mmol). The pH was adjusted to 7.5 with triethylamine. After 16 h, the reaction was poured into water and extracted with ethyl acetate. The organic phase was washed with saturated brine and dried over magnesium sulfate. The crude product was chromatographed on silica gel with 10% methanol in methylene chloride. The purified product was converted to the hydrochloride salt with 4N HCl in dioxane. The title compound was obtained as a white solid. FAB ms (m+1) 428.

Anal. Calc. for $C_{25}H_{25}N_5O_2 \cdot 0.55\ H_2O$: C, 63.37; H, 5.76; N, 14.78. Found: C, 63.37; H, 6.05; N, 13.28.

Example 2

3-[3-{1-(4-Cyanobenzyl)-5-imidazolyl}-1-propyl]1-phenyl-2-piperidinone hydrochloride

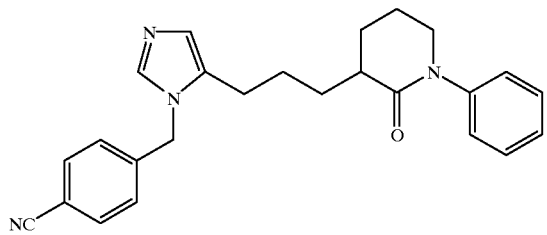

Step A: Methyl 3-(4-imidazolyl)-2-propenoate

A suspension of urocanic acid (5.0 g) in methanol at 0° C. was saturated with HCl gas. The reaction was stirred for one hour, then concentrated in vacuo to dryness to provide the title compound

Step B: Methyl 3-(4-imidazolyl)propionate

To a solution of methyl 3-(4-imidazolyl)-2-propenoate (5.3 g) in methanol a t room temperature was added 10% palladium on carbon (20 mg) under a blanket of argon. A balloon of hydrogen was applied, and the reaction was stirred for one hour. The solution was filtered, and then concentrated in vacuo to dryness to provide the title compound.

Step C: Methyl 3-(1-triphenylmethyl-4-imidazolyl)propionate p To a solution of methyl 3-(4-imidazolyl)propionate (1.77 g) in 10 mL of dry DMF at room temperature was added triethylamine (3.25 mL). A white solid precipitated from the solution. Chlorotriphenylmethane (2.65 g) in 12 mL of DMF was added dropwise. The reaction mixture was stirred for 20 hours, then poured into 40% ethyl acetate/hexane solution and washed with two portions of water. The organic layer was extracted with sat. aq. $NaHCO_3$ solution and brine, then dried ($Na_2SO_4$), filtered, and concentrated in vacuo to provide the title compound.

Step D: 4-(3-Hydroxy-1-propyl)-3-(1-triphenylmethyl-4-imidazolyl)propionate

The product from Step C (0.063 g, 0.159 mmol) was dissolved in THF and cooled to 0° C. under nitrogen. A solution of lithium aluminum hydride in THF (1 M, 0.180 mL) was added and the reaction stirred at 0° C. for 20 min. The reaction was quenched with saturated sodium potassium tartrate solution and extracted with ethyl acetate. The title compound was obtained as a clear oil.

Step E: 1-Phenyl-2-piperdinone

A mixture of valerolactam (1.00 g, 10.18 mmol), triphenylbismuth (6.72 g, 15.27 mmol), copper(II)acetate (2.77 g, 15.27 mmol) and triethylamine (2.12 mL, 15.27 mmol) was stirred for 17 h at 20° C. in dichloromethane (25 mL). The reaction mixture was adsorbed onto silica gel and chromatographed with 40% ethyl acetate/methylene chloride. The title compund was obtained as an oil.

Step F: 3-[3-{1-triphenylmethyl-4-imidazolyl}-1-propyl]-1-phenyl-2-piperidinone hydrochloride A solution of 1-phenyl-2-piperidinone from Step F in THF is added to a solution of one equivalent of LDA in THF at −78° C., and stirred for 30 min. A solution of 4-(3-hydroxy-1-propyl)-3-(1-triphenylmethyl-4—imidazolyl) propionate in methylene chloride is cooled to −78° C. under nitrogen. One equivalent of n-butyl lithium followed by one equivalent of triflic anhydride is added, the reaction stirred for 10 min, then added to the LDA/1-phenyl-2-piperidinone solution. The reaction is warmed to room temperature, and quenched with saturated ammonium chloride. The reaction is then partitioned between ethyl acetate and saturated brine. The organic phase is dried over magnesium sulfate, filtered and concentrated. The title compound is isolated by chromatography on silica gel.

Step G: 3-[3-{1-(4-Cyanobenzyl)-5-imidazolyl}-1-propyl]-1-phenyl-2-piperidinone hydrochloride The product from Step F is dissolved in acetonitrile and one equivalent of 4-cyanobenzylbromide added. The reaction is stirred at room temperature overnight, concentrated, and taken up in methanol. The methanol solution is refluxed for 3 h, concentrated, and partitioned between ethyl acetate and saturated sodium bicarbonate solution. The organic phase is washed with saturated brine and dried over magnesium sulfate. The title compound is obtained after chromatography on silica gel, and conversion to the dihydrochloride salt.

Example 3

3-[3-{1-(4-Cyanobenzyl)-5-imidazolyl }-1-propyl]-1-phenyl-2-pyrrolidinone hydrochloride

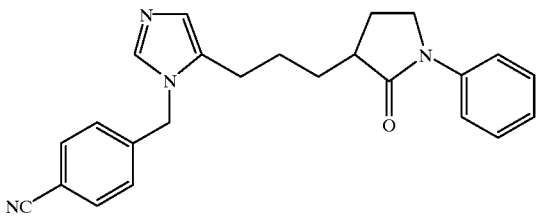

Step A: 1-Phenyl-2-pyrrolidinone

The title compound is prepared according to the procedure described in Example 2, Step E, except using 2-pyrrolidinone in place of valerolactam. The crude product is purified by column chromatography.

Step B: 3-[3-{1-triphenylmethyl-4-imidazolyl}-1-propyl]-1-phenyl-2-pyrrolidinone The title compound is prepared according to the procedure described in Example 2, Step F, except using 1-phenyl-2-pyrrolidinone in place of 1-phenyl-2-piperdinone. The title compound is isolated by chromatography on silica gel.

Step C: 3-[3-{1-(4-Cyanobenzyl)-5-imidazolyl}-1-propyl]-1-phenyl-2-pyrrolidinone hydrochloride The title compound is prepared according to the procedure described in Example 2, Step G except using 3-[3-{1-triphenylmethyl-4-imidazolyl}-1-propyl]-1-phenyl-2-pyrrolidinone in place of 3-[3-{1-triphenylmethyl-4-imidazolyl}-1-propyl]-1-phenyl-2-piperidinone. The title compound is obtained after chromatography on silica gel, and conversion to the hydrochloride salt.

Example 4

(±)cis- and (±)trans-3-[3-{1-(4-Cyanobenzyl)-5-imidazolyl}-1-propyl]-4-methoxymethyl-1-phenyl-2-pyrrolidinone hydrochloride

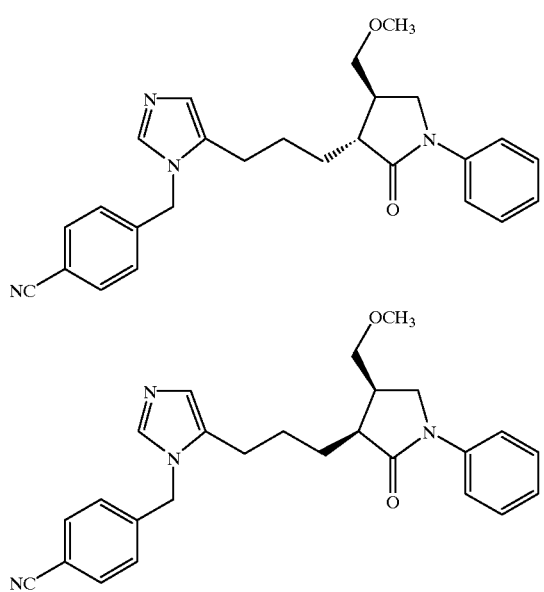

Step A: 4-Carbomethoxy-1-phenyl-2-pyrrolidinone

Commercially available 4-carboxy-1-phenyl-2-pyrrolidinone in 10% methanol in toluene is treated with an excess of trimethylsilyldiazomethane for 30 min. Excess diazomethane reagent is destroyed with glacial acetic acid. The solvents are removed in vacuo and the title compound is isolated.

Step B: 4-Hydroxymethyl-1-phenyl-2-pyrrolidinone

The product from Step A in THF is added to a 0° C. solution of 2.5 eq lithium aluminum hydride in THF, under a nitrogen atmosphere. After 30 min the reaction is quenched with sodium hydrogen sulfate, and filtered through a bed of celite. The filtrate is concentrated and the residue partitioned between 2% aqueous sodium hydrogen sulfate and ethyl acetate. The organic layer is washed with saturated brine and dried over magnesium sulfate. Filtration and concentration provides the title compound.

Step C: 4-Methoxymethyl-1-phenyl-2-pyrrolidinone

The product from Step C in THF is added to 1.5 eq sodium hydride and 1 eq methyl iodide in THF at 0° C. After 3 h the reaction is quenched with water and extracted with ethyl acetate. The ethyl acetate is washed with saturated brine, dried over magnesium sulfate, filtered and concentrated. The title compound is isolated after column chromatography.

Step D: (±)cis- and (±)trans-4-Methoxymethyl-1-phenyl-3-[3-{1-t riphenylmethyl-4-imidazolyl}-1-propyl]-2-pyrrolidinone The title compound is prepared according to the procedure described in Example 2, Step F, except using 4-methoxymethyl-1-phenyl-2-pyrrolidinone in place of 1-phenyl-2-piperdinone. The title compounds are isolated by chromatography on silica gel.

Step E: (±)cis- and (±)trans-3-[3-{1-(4-Cyanobenzyl)-5-imidazolyl}-1-propyl]-4-methoxymethyl-1-phenyl-2pyrrolidinone hydrochloride The title compound is prepared according to the procedure described in Example 2, Step G except using (cis -and trans-4-methoxymethyl-1-phenyl-3-[3-{1-triphenylmethyl-4-imidazolyl }-1-propyl]-2-pyrrolidinone in place of 3-[3-{1-triphenylmethyl-4-imidazolyl}-1-propyl]-1-phenyl-2-piperidinone. The title compounds are separated by preparative HPLC and converted to their hydrochloride salts.

Example 5

3-[2-{5-(4-Cyanobenzyl)-1-imidazolyl}-1-ethyl]-1-phenyl-2-pyrrolidinone hydrochloride

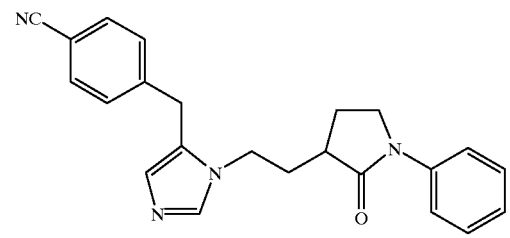

Step A: N-Phenyl 4-chlorobutyramide

A solution of aniline (10.0 mL, 110 mmol) and triethylamine (18.4 mL, 132 mmol) in methylene chloride (100 mL) was cooled to 0° C. under argon, and 4-chlorobutyrylchloride (14.8 mL, 132 mmol) added dropwise. The reaction was stirred at room temperature for 1.5 h, then extracted with 1M potassium hydrogen sulfate. The organic phase was separated, washed with saturated brine, and dried over sodium sulfate. After concentration in vacuo, the white solid was triturated with hexane and filtered, giving the title compound.

Step B: 1-Phenyl-2-pyrrolidinone

The product from Step A (21.7 g, 110 mmol) was dissolved in THF (157 mL) under argon, and sodium hydride (60% dispersion in oil) (5.01 g, 125 mmol) added slowly portionwise. The reaction was stirred at room temperature overnight. An additional portion of sodium hydride was added (1 g) and the reaction continued to stir for 3 h. The reaction was diluted with ethyl acetate and poured into 10% aqueous hydrogen chloride. The organic phase was washed with saturated brine, and dried over sodium sulfate. Concentration in vacuo afforded the title compound.

Step C: 3-(t-Butylcarboxymethyl)-1-phenyl-2-pyrrolidinone

Diisopropylamine (0.722 mL, 41.0 mmol) in THF 950 mL) was cooled under argon to —78° C. and a solution of n-butyllithium in hexane (15.1 mL of 2.5 M solution, 37.8 mmol) was added. After stirring at 0° C. for 15 min, this solution was transferred via cannula to a −78° C. solution of the product from Step B (5.09 g, 31.5 mmol) in THF (108 mL). When the addition was complete, the reaction was stirred at 0° C. for 1 h, then cooled to −78° C. and t-butyl bromoacetate (5.12 mL, 34.7 mmol) added via syringe. The reaction was stirred at −78° C. for 2 h, then allowed to warm to room temperature overnight. The reaction was quenched with 10% aqueous HCl and extracted with ethyl acetate. The organic layer was washed with saturated brine and dried over sodium sulfate. The title compound was obtained after chromatography on silica gel with 20% ethyl acetate in hexane.

Step D: 3-(2-Carboxymethyl)-1-phenyl-2-pyrrolidinone

The product from Step C (2.37 g, 8.60 mmol) was stirred in methylene chloride containing 2% water and 10% trifluoroacetic acid (60 mL). Subsequently, additional water (1 mL) and trifluoroacetic acid (5 mL) was added and the reaction stirred at room temperature overnight. The solvent was removed in vacuo, and the residue partitioned between saturated ammonium chloride and ethyl acetate. The combined organic layers were washed with saturated brine, and dried over sodium sulfate. Filtration and evaporation of solvent gave the title compound.

Step E: 3-(2-Hydroxyethyl)-1-phenyl-2-pyrrolidinone

Ethyl chloroformate (0.201 mL, 2.10 mmol) was added to a 0° C. solution of triethylamine (0.294 mL, 2.10 mmol) and the product from Step D (0.420 g, 1.91 mmol) in THF (10 mL). The reaction was stirred for 1.5 h, and sodium borohydride added (0.217 g, 5.74 mmol). The reaction was stirred at room temperature overnight, then quenched with saturated sodium bicarbonate solution. The layers were separated and the aqueous phase extracted with additional ethyl acetate. The combined organic phases were washed with saturated brine and dried over sodium sulfate. The title compound was obtained after purification on silica gel with 0–70% ethyl acetate in hexane.

Step F: 1-Trityl-4-(4-cyanobenzyl)-imidazole.

To a suspension of activated zinc dust (3.57 g, 54.98 mmol) in THF (50 mL) was added dibromoethane (0.315 mL, 3.60 mmol) and the reaction stirred under argon at 20° C. The suspension was cooled to 0° C and α-bromo-p-toluinitrile (9.33 g, 47.6 mmol) in THF (100 mL) was added dropwise over a period of 10 min. The reaction was then allowed to stir at 20° C. for 6 h and bis(triphenylphosphine) Nickel II chloride (2.4 g, 3.64 mmol) and 4-iodotrityl imidazole (15.95 g, 36.6 mmol) was added in one portion. The resulting mixture was stirred 16 h at 20° C. and then quenched by addition of saturated ammonium chloride solution (100 mL) and the mixture stirred for 2 h. Saturated sodium bicarbonate solution was added to give a pH of S and the solution was extracted with ethyl acetate (2×250 mL), dried with magnesium sulfate, and the solvent evaporated in vacuo. The residue was chromatographed on silica gel with 0–20% ethyl acetate in methylene chloride to afford the title compound as a white solid.

$^1$H NMR δ CDCl$_3$ (7.54 (2H,d, J=7.9 Hz), 7.38(1H,s), 7.36–7.29 (11H,m), 7.15–7.09(6H,m), 6.58(1H,s), and 3.93 (2H,s))ppm.

Step G: 3-[2-{5-(4-Cyanobenzyl)-1-imidazolyl}-1-ethyl]-1-phenyl-2-pyrrolidinone hydrochloride A solution of the products from Step E (0.100 g, 0.487 mmol) and Step F (0.207 g, 0.487 mmol) and diisopropylethyl amine (0.094 mL, 0.535 mmol) in methylene chloride (2 mL) was cooled to -78° C. under argon. Trifluoromethanesulfonic acid anhydride (0.084 mL, 0.501 mmol) was added and the reaction warmed to room temperature over a period of two hours. The reaction was stirred at room temperature overnight, and then the solvent removed in vacuo. The residue was dissolved in methanol (3 mL) and refluxed for 2 h. The methanol was evaporated, and the residue partitioned between ethyl acetate and saturated sodium bicarbonate solution. The organic phase was washed with saturated brine, and dried over sodium sulfate. The crude product was chromatographed on silica gel with 50% acetone in methylene chloride followed by 10% methanol in chloroform. The title compound was obtained after conversion to the HCl salt. FAB ms: 371 (M+1). Anal. Calc for $C_{23}H_{22}N_4O.1.55$ HCl.0.30 $H_2O$, C, 63.89; H, 5.63; N,12.96. Found: C, 63.88; H, 5.64; N, 12.82.

Example 6

1-Benzyl-3-[2-{5-(4-cyanobenzyl)-1-imidazolyl}-1-ethyl]-2-pyrrolidinone hydrochloride

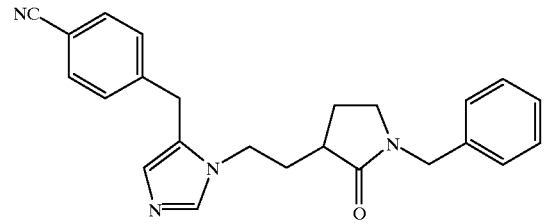

Step A: N-Benzyl 4-chlorobutyramide

The title compound was prepared according to the procedure described in Example 5, Step A, using benzylamine in place of aniline.

Step B: 1-Benzyl-3-[2-{5-(4-cyanobenzyl)-1-imidazolyl}-1-ethyl]-2-pyrrolidinone hydrochloride Using the product of Step A, the title compound was prepared according to the procedure described in Example 5, Steps B–G. FAB ms: 385 (M+1). Anal. Calc for $C_{24}H_{24}N_4O.2.3$ HCl.0.60 $Et_2O$, C, 61.83; H, 6.35; N,10.93. Found: C, 61.85; H, 5.97; N, 10.61.

Example 7

Preparation of (±)-1-(3-chloropheny)-3-[1-(1-(4-cyanobenzyl)-5-imidazolyl)-1-(hydroxy)methyl]-2-piperazinone hydrochloride Step A: Preparation of 1-triphenylmethyl-4-(hydroxymethyl)-imidazole To a solution of 4-(hydroxymethyl)imidazole hydrochloride (35.0 g, 260 mmol) in 250 mL of dry DMF at room temperature was added triethylamine (90.6 mL, 650 mmol). A white solid precipitated from the solution. Chlorotriphenylmethane (76.1 g, 273 mmol) in 500 mL of DMF was added dropwise. The reaction mixture was stirred for 20 hours, poured over ice, filtered, and washed with ice water. The resulting product was slurried with cold dioxane, filtered, and dried in vacuo to provide the titled product as a white solid which was sufficiently pure for use in the next step.

Step B: Preparation of 1-triphenylmethyl-4-(acetoxymethyl)-imidazole

Alcohol from Step A (260 mmol, prepared above) was suspended in 500 mL of pyridine. Acetic anhydride (74 mL, 780 mmol) was added dropwise, and the reaction was stirred for 48 hours during which it became homogeneous. The solution was poured into 2 L of EtOAc, washed with water (3×1 L), 5% aq. HCl soln. (2×1 L), sat. aq. $NaHCO_3$, and brine, then dried ($Na_2SO_4$), filtered, and concentrated in vacuo to provide the crude product. The acetate was isolated as a white powder which was sufficiently pure for use in the next reaction.

Step C: Preparation of 1-(4-cyanobenzyl)-5-(acetoxymethyl)-imidazole hydrobromide A solution of the product from Step B (85.8 g, 225 mmol) and α-bromo-p-tolunitrile (50.1 g, 232 mmol) in 500 mL of EtOAc was stirred at 60° C. for 20 hours, during which a pale yellow precipitate formed. The reaction was cooled to room temperature and filtered to provide the solid imidazolium bromide salt. The filtrate was concentrated in vacuo to a volume 200 mL, reheated at 60 ° C. for two hours, cooled to room temperature, and filtered again. The filtrate was concentrated in vacuo to a volume 100 mL, reheated at 60 ° C. for another two hours, cooled to room temperature, and concentrated in vacuo to provide a pale yellow solid. All of the solid material was combined, dissolved in 500 mL of methanol, and warmed to 60° C. After two hours, the solution was reconcentrated in vacuo to provide a white solid which was triturated with hexane to remove soluble materials. Removal of residual solvents in vacuo provided the titled product hydrobromide as a white solid which was used in the next step without further purification.

Step D: Preparation of 1-(4-cyanobenzyl)-5-(hydroxymethyl)-imidazole

To a solution of the acetate from Step C (50.4 g, 150 mmol) in 1.5 L of 3:1 THF/water at 0° C. was added lithium hydroxide monohydrate (18.9 g, 450 mmol). After one hour, the reaction was concentrated in vacuo, diluted with EtOAc (3 L), and washed with water, sat. aq. $NaHCO_3$ and brine. The solution was then dried ($Na_2SO_4$), filtered, and concentrated in vacuo to provide the crude product as a pale yellow fluffy solid which was sufficiently pure for use in the next step without further purification.

Step E: Preparation of 1-(4-cyanobenzyl)-5-imidazolecarboxaldehyde

To a solution of the alcohol from Step D (21.5 g, 101 mmol) in 500 ml, of DMSO at room temperature was added triethylamine (56 mL, 402 mmol), then $SO_3$-pyridine complex (40.5 g, 254 mmol). After 45 minutes, the reaction was poured into 2.5 L of EtOAc, washed with water (4×1 L) and brine, dried ($Na_2SO_4$), filtered, and concentrated in vacuo to provide the aldehyde as a white powder which wits sufficiently pure for use in the next step without further purification.

Step F: Preparation of N-(3-chlorophenyl)ethylenediamine hydrochloride

To a solution of 3-chloroaniline (30.0 mL, 284 mmol) in 500 mL of dichloromethane at 0° C. was added dropwise a solution of 4 N HCl in 1,4-dioxane (80 mL, 320 mmol HCl). The solution was warmed to room temperature, then concentrated to dryness in vacuo to provide a white powder. A mixture of this powder with 2-oxazolidinone (24.6 g, 282 mmol) was heated under nitrogen atmosphere at 160° C. for 10 hours, during which the solids melted, and gas evolution was observed. The reaction was allowed to cool, forming the crude diamine hydrochloride salt as a pale brown solid.

Step G: Preparation of N-(tert-butoxycarbonyl)-N'-(3-chlorophenyl)ethylenediamine The amine hydrochloride from Step F (ca. 282 mmol, crude material prepared above) was taken up in 500 mL of THF and 500 mL of sat. aq. $NaHCO_3$ soln., cooled to 0° C., and di-tert-butylpyrocarbonate (61.6 g, 282 mmol) was added. After 30 h, the reaction was poured into EtOAc, washed with water and brine, dried ($Na_2SO_4$), filtered, and concentrated in vacuo to provide the titled carbamate as a brown oil which was used in the next step without further purification.

Step H: Preparation of N-[2-(tert-butoxycarbamoyl)ethyl]-N-(3-chlorophenyl)-2-chloroacetamide A solution of the product from Step G (77 g, (a. 282 mmol) and triethylamine (67 mL, 480 mmol) in 500 mL of $CH_2Cl_2$ was cooled to 0 ° C. Chloroacetyl chloride (25.5 mL, 320 mmol) was added dropwise, and the reaction was maintained at 0° C. with stirring. After 3 h, another portion of chloroacetyl chloride (3.0 mL) was added dropwise. After 30 min, the reaction was poured into EtOAc (2 L) and washed with water, sat. aq. $NH_4Cl$ soln, sat. aq. $NaHCO_3$ soln., and brine. The solution was dried ($Na_2SO_4$), filtered, and concentrated in vacuo to provide the chloroacetamide as a brown oil which was used in the next step without further purification.

Step I: Preparation of 4-(tert-butoxycarbonyl)-1-(3-chlorophenyl)-2-piperazinone To a solution of the chloroacetamide from Step H (ca. 282 mmol) in 700 mL of dry DMF was added $K_2CO_3$ (88 g, 0.64 mol). The solution was heated in an oil bath at 70–75 ° C. for 20 hours, cooled to room temperature, and concentrated in vacuo to remove ca. 500 mL of DMF. The remaining material was poured into 33% EtOAc/hexane, washed with water and brine, dried ($Na_2SO_4$), filtered, and concentrated in vacuo to provide the product as a brown oil. This material was purified by silica gel chromatography (25–50% EtOAc/hexane) to yield pure titled product.

Step J: Preparation of (±)-4-(tert-butoxycarbonyl)-1-(3-chloropheny)-3-[1-(1-(4-cyanobenzyl)-5-imidazolyl)-1-(hydroxy)methyl]-2-piperazinone To a solution of the piperazinone from Step I (98.0 mg, 0.316 mmol) in 1.5 mL of THF at −78 ° C. was added dropwise 1M lithium hexamethyldisilazide solution (0.332 mL, 0.332 mmol). After 20 minutes. a solution of the aldehyde from Step E (76 mg, 0.360 mmol) in 0.5 mL of THF was added. After 30 min, the reaction was quenched with sat aq. NH4Cl soln., poured into EtOAc, and washed with sat. aq. $NaHCO_3$ soln., and brine. The solution was dried ($Na_2SO_4$), filtered, and concentrated in vacuo to provide the crude product. The product was purified by flash chromatography on silica gel (3–6% MeOH/CH2Cl2) to provide 60 mg of the titled product as a 9:1 mixture of diastereomers.

Step K: Preparation of (±)-1-(3-chloropheny)-3-[1-(1-(4-cyanobenzyl)-5-imidazolyl)-1-(hydroxy)methyl]2-piperazinone hydrochloride To a solution of the piperazinone from Step J (60 mg, 0.115 mmol) in 2 mL of dichloromethane at 0° C. was added trifluoroacetic acid (1.0 mL), and the reaction was allowed to warm to room temperature. After 6 hours, the solution was concentrated in vacuo, taken up in CH2Cl2, washed with dilute aq. NaHCO₃ soln., dried (Na₂SO₄), filtered, and concentrated in vacuo to provide the crude product. After conversion to the HCl salt, the product was isolated (62 mg) as a 9:1 mixture of diastereomers. FAB ms: 422 (M+1). Anal. Calc for C22H20ClN5O2.2.10 HCl. 1.00 H₂O: C, 51.16; H, 4.70; 0, 13.56. Found: C, 51.21; H, 4.70; 0, 12.66.

Example 8
In vitro inhibition of ras farnesyl transferase
Assays of farnesyl-protein transferase. Partially purified bovine FPTase and Ras peptides (Ras-CVLS, Ras-CVIM and Ras-CAIL) were prepared as described by Schaber et al., *J. Biol. Chem.* 265:14701–14704 (1990), Pompliano, et al., *Biochemistry* 31:3800 (1992) and Gibbs et al., *PNAS U.S.A.* 86:6630–6634 (1989), respectively. Bovine FPTase was assayed in a volume of 100 µl containing 100 mM N-(2-hydroxy ethyl) piperazine-N'-(2-ethane sulfonic acid) (HEPES), pH 7.4, 5 mM MgCl₂, 5 mM dithiothreitol (DTT), 100 mM [³H]-farnesyl diphosphate ([³H]-FPP; 740 CBq/mmol, New England Nuclear), 650 nM Ras-CVLS and 10 µg/ml FPTase at 31° C. for 60 min. Reactions were initiated with FPTase and stopped with 1 ml of 1.0 M HCL in ethanol. Precipitates were collected onto filter-mats using a Tom Tec Mach II cell harvester, washed with 100% ethanol, dried and counted in an LKB P-plate counter. The assay was linear with respect to both substrates, FPTase levels and time; less than 10% of the [³H]-FPP was utilized during the reaction period. Purified compounds were dissolved in 100% dimethyl sulfoxide (DMSO) and were diluted 20-fold into the assay. Percentage inhibition is measured by the amount of incorporation of radioactivity in the presence of the test compound when compared to the amount of incorporation in the absence of the test compound.

Human FPTase was prepared as described by Omer et al., *Biochemistry* 32:5167–5176 (1993). Human FPTase activity was assayed as described above with the exception that 0.1% (w/v) polyethylene glycol 20,000, 10 µM ZnCl₂ and 100 nM Ras-CVIM were added to the reaction mixture. Reactions were performed for 30 min., stopped with 100 µl of 30% (v/v) trichloroacetic acid (TCA) in ethanol and processed as described above for the bovine enzyme.

The compounds of the instant invention described in the above Examples 1 and 5–7 were tested for inhibitory activity against human FPTase by the assay described above and were found to have IC₅₀ of ≤50 µM.

Example 9
In vivo ras farnesylation assay
The cell line used in this assay is a v-ras line derived from either RatI or NIH3T3 cells, which expressed viral Ha-ras p21. The assay is performed essentially as described in DeClue, J. E. et al., *Cancer Research* 51:712–717, (1991). Cells in 10 cm dishes at 50–75% confluency are treated with the test compound (final concentration of solvent, methanol or dimethyl sulfoxide, is 0.1%). After 4 hours at 37° C., the cells are labelled in 3 ml methionine-free DMEM supplemeted with 10% regular DMEM, 2% fetal bovine serum and 400 mCi[³⁵S]methionine (1000 Ci/mmol). After an additional 20 hours, the cells are lysed in 1 ml lysis buffer (1% NP40/20 mM HEPES, pH 7.5/5 mM MgCl₂/1 mM DTT/10 mg/ml aprotinen/2 mg/ml leupeptin/2 mg/ml antipain/0.5 mM PMSF) and the lysates cleared by centrifugation at 100,000×g for 45 min. Aliquots of lysates containing equal numbers of acid-precipitable counts are bought to 1 ml with IP buffer (lysis buffer lacking DTT) and immunoprecipitated with the ras-specific monoclonal antibody Y13-259 (Furth, M. E. et al., *J. Virol.* 43:294–304, (1982)). Following a 2 hour antibody incubation at 4° C., 200 ml of a 25% suspension of protein A-Sepharose coated with rabbit anti rat IgG is added for 45 min. The immunoprecipitates are washed four times with IP buffer (20 nM HEPES, pH 7.5/1 mM EDTA/1% Triton X-100.0.5% deoxycholate/0.1%/SDS/0.1 M NaCl) boiled in SDS-PAGE sample buffer and loaded on 13% acrylamide gels. When the dye front reached the bottom, the gel is fixed, soaked in Enlightening, dried and autoradiographed. The intensities of the bands corresponding to farnesylated and nonfarnesylated ras proteins are compared to determine the percent inhibition of farnesyl transfer to protein.

Example 10
In vivo growth inhibition assay
To determine the biological consequences of FPTase inhibition, the effect of the compounds of the instant invention on the anchorage-independent growth of Rat 1 cells transformed with either a v-ras, v-raf, or v-mos oncogene is tested. Cells transformed by v-Raf and v-Mos maybe included in the analysis to evaluate the specificity of instant compounds for Ras-induced cell transformation.

Rat 1 cells transformed with either v-ras, v-raf, or v-mos are seeded at a density of 1×10⁴ cells per plate (35 mm in diameter) in a 0.3% top agarose layer in medium A (Dulbecco's modified Eagle's medium supplemented with 10% fetal bovine serum) over a bottom agarose layer (0.6%). Both layers contain 0.1% methanol or an appropriate concentration of the instant compound (dissolved in methanol at 1000 times the final concentration used in the assay). The cells are fed twice weekly with 0.5 ml of medium A containing 0.1% methanol or the concentration of the instant compound. Photomicrographs are taken 16 days after the cultures are seeded and comparisons are made.

What is claimed is:
1. A compound which inhibits farnesyl-protein transferase of the formula A:

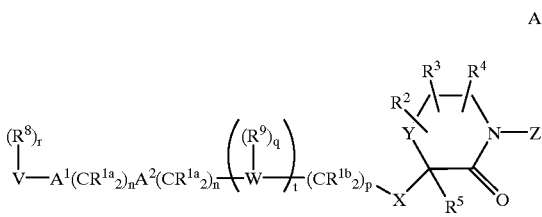

A wherein:
R¹ᵃ and R¹ᵇ are independently selected from:
a) hydrogen,
b) aryl, heterocycle, C₃–C₁₀ cycloalkyl, C₂–C₆ alkenyl, C₂–C₆ alkynyl, R¹⁰O—, R¹¹S(O)ₘ—, R¹⁰C(O)NR $^{10}$—, $CN(R^{10})_2NC(O)$—, $R^{10}{}_2N$—$C(NR^{10})$—, CN, NO$_2$, $R^{11}C(O)$—, N$_3$, —N(R$^{10}$)$_2$, or $R^{11}OC(O)NR^{10}$—, c) unsubstituted or substituted C$_1$–C$_6$ alkyl wherein the substitutent on the substituted C$_1$–C$_6$ alkyl is selected from unsubstituted or substituted aryl, heterocyclic, C$_3$–C$_{10}$ cycloalkyl, C$_2$–C$_6$ alkenyl, C$_2$–C$_6$ alkynyl, $R^{10}O$—, $R^{11}S(O)_m$—, $R^{10}C(O)NR^{10}$—, $(R^{10})_2NC(O)$—, $R^{10}{}_2N$—$C(NR^{10})$—, CN, $R^{10}C(O)$—, N$_3$, —N(R$^{10}$)$_2$, and $R^{11}OC(O)$—NR$^{10}$—;

R$^2$ and R$^4$ are independently selected from: H; unsubstituted or substituted C$_{1-8}$ alkyl, unsubstituted or substituted C$_{2-8}$ alkenyl, unsubstituted or substituted C$_{2-8}$ alkynyl, unsubstituted or substituted aryl, unsubstituted or substituted heterocycle,

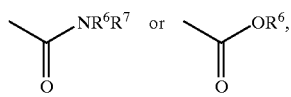

wherein the substituted group is substituted with one or more of:
1) aryl or heterocycle, unsubstituted or substituted with:
   a) C$_{1-4}$ alkyl,
   b) (CH$_2$)$_p$OR$^6$,
   c) (CH$_2$)$_p$NR$^6$R$^7$,
   d) halogen,
   e) CN,
   f) aryl or heteroaryl,
   g) perfluoro-C$_{1-4}$ alkyl,
   h) SR$^{6a}$, S(O)R$^{6a}$, SO$_2$R$^{6a}$,
2) C$_{3-6}$ cycloalkyl,
3) OR$^6$,
4) SR$^{6a}$, S(O)R$^{6a}$, or SO$_2$R$^{6a}$,
5) —NR$^6$R$^7$

5) —NR$^6$R$^7$,

6) 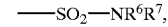

7) 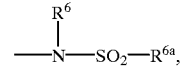

8) 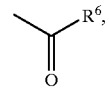

9) 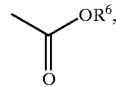

-continued

10) 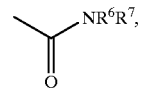

11) —SO$_2$—NR$^6$R$^7$,

12)

13)

14)

15) N$_3$,
16) F, or
17) perfluoro-C$_{1-4}$-alkyl; or

R$^3$ and R$^5$ are selected from H and CH$_3$;
R$^2$ and R$^3$ or R$^4$ and R$^5$ are attached to the same C atom and are combined to form —(CH$_2$)$_u$— wherein one of the carbon atoms is optionally replaced by a moiety selected from: O, S(O)$_m$, —NC(O)—, and —N(COR$^{10}$) ;

R$^6$, R$^7$ and R$^{7a}$ are independently selected from: H; C$_{1-4}$ alkyl, C$_{3-6}$ cycloalkyl, heterocycle, aryl, aroyl, heteroaroyl, arylsulfonyl, heteroarylsulfonyl, unsubstituted or substituted with:
a) C$_{1-4}$ alkoxy,
b) aryl or heterocycle,
c) halogen,
d) HO,
e) 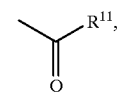

f) —SO$_2$R$^{11}$, or
g) N(R$^{10}$)$_2$; or

R$^6$ and R$^7$ may be joined in a ring;
R$^7$ and R$^{7a}$ may be joined in a ring;
R$^{6a}$ is selected from: C$_{1-4}$ alkyl, C$_{3-6}$ cycloalkyl, heterocycle, aryl, unsubstituted or substituted with:
a) C$_{1-4}$ alkoxy,
b) aryl or heterocycle,
c) halogen,
d) HO,
e) 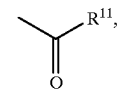

f) —SO$_2$R$^{11}$, or
g) N(R$^{10}$)$_2$;

$R^8$ is independently selected from:
a) hydrogen,
b) aryl, heterocycle, $C_3$–$C_{10}$ cycloalkyl, $C_2$–$C_6$ alkenyl, $C_2$–$C_6$ alkynyl, perfluoroalkyl, F, Cl, Br, $R^{10}$—, $R^{11}S(O)_m$—, $R^{10}C(O)NR^{10}$, $(R^{10})_2NC(O)$—, $R^{10}_2N$—C($NR^{10}$)—, CN, $NO_2$, $R^{10}C(O)$—, $N_3$, —$N(R^{10})_2$, or $R^{11}OC(O)NR^{10}$—, and
c) $C_1$–$C_6$ alkyl unsubstituted or substituted by aryl, cyanophenyl, heterocycle, $C_3$–$C_{10}$ cycloalkyl, $C_2$–$C_6$ alkenyl, $C_2$–$C_6$ alkynyl, perfluoroalkyl, F, Cl, Br, $R^{10}O$—, $R^{11}S(O)_m$—, $R^{10}C(O)NH$—, $(R^{10})_2NC(O)$—, $R^{10}_2N$—C($NR^{10}$)—, CN, $R^{10}C(O)$—, $N_3$, —$N(R^{10})_2$, or $R^{10}C(O)NH$—;

$R^9$ is selected from:
a) hydrogen,
b) alkenyl, alkynyl, perfluoroalkyl, F, Cl, Br, $R^{10}O$—, $R^{11}S(O)_m$—, $R^{10}C(O)NR^{10}$—, $(R^{10})_2NC(O)$—, $R^{10}_2N$—C($NR^{10}$)—, CN, $NO_2$, $R^{10}C(O)$—, $N_3$, —$N(R^{10})_2$, or $R^{10}OC(O)NR^{10}$—, and
c) $C_1$–$C_6$ alkyl unsubstituted or substituted by perfluoroalkyl, F, Cl, Br, $R^{10}$ O—, $R^{11}S(O)_m$—, $R^{10}C(O)NR^{10}$—, $(R^{10})_2NC(O)$—, $R^{10}_2N$—C($NR^{10}$)—, CN, $R^{10}C(O)$—, $N_3$, —$N(R^{10})_2$, or $R^{11}OC(O)NR^{10}$—;

$R^{10}$ is independently selected from hydrogen, $C_1$–$C_6$ alkyl, benzyl and aryl;
$R^{11}$ is independently selected from $C_1$–$C_6$ alkyl and aryl;
$A^1$ and $A^2$ are independently selected from: a bond, —CH=CH—, —C≡C—, —C(O)—, —C(O)$NR^{10}$—, —$NR^{10}$C(O)—, O, —N($R^{10}$)—, —S(O)$_2$N($R^{10}$)—, —N($R^{10}$)S(O)$_2$—, or S(O)$_m$;

V is selected from:
a) hydrogen,
b) heterocycle,
c) aryl,
d) $C_1$–$C_{20}$ alkyl wherein from 0 to 4 carbon atoms are replaced with a a heteroatom selected from O, S, and N, and
e) $C_2$–$C_{20}$ alkenyl,
provided that V is not hydrogen if $A^1$ is S(O)$_m$ and V is not hydrogen if $A^1$ is a bond, n is 0 and $A^2$ is S(O)$_m$;

W is a heterocycle;
X is a bond, —$CH_2$—, —C(=O)—, —C(O)$NR^6$—, —$NR^6$C(O)—, —$NR^6$— or —S(=O)$_m$—;
Y is a bond, —$CH_2$—, —NH—, —S(=O)$_m$— or O;
Z is selected from:
1) a unsubstituted or substituted group selected from aryl, heteroaryl, arylmethyl, heteroarylmethyl, arylsulfonyl, heteroarylsulfonyl, wherein the substituted group is substituted with one or more of the following:
   a) $C_{1-4}$ alkyl, unsubstituted or substituted with: $C_{1-4}$ alkoxy, $NR^6R^7$, $C_{3-6}$ cycloalkyl, aryl, heterocycle, HO, —S(O)$_m R^{6a}$, or —C(O)$NR^6R^7$,
   b) aryl or heterocycle,
   c) halogen,
   d) $OR^6$,
   e) $NR^6R^7$,
   f) CN,
   g) $NO_2$,
   h) $CF_3$;
   i) —S(O)$_m R^{6a}$,
   j) —C(O)$NR^6R^7$, or
   k) $C_3$–$C_6$ cycloalkyl; or
2) unsubstituted $C_1$–$C_6$ alkyl, substituted $C_1$–$C_6$ alkyl, unsubstituted $C_3$–$C_6$ cycloalkyl or substituted $C_3$–$C_6$ cycloalkyl, wherein the substituted $C_1$–$C_6$ alkyl and substituted $C_3$–$C_6$ cycloalkyl is substituted with one or two of the following:
   a) $C_{1-4}$ alkoxy,
   b) $NR^6R^7$,
   c) $C_{3-6}$ cycloalkyl,
   d) —$NR^6C(O)R^7$,
   e) HO,
   f) —S(O)$_m R^{6a}$,
   g) halogen, or
   h) perfluoroalkyl;

m is 0, 1 or 2;
n is 0, 1, 2, 3 or 4;
p is 0, 1, 2, 3 or 4;
q is 1 or 2;
r is 0 to 5, provided that r is 0 when V is hydrogen;
t is 1; and
u is 4 or 5;
or a pharmaceutically acceptable salt thereof.

2. The compound according to claim 1 of the formula A wherein Y is a bond, —$CH_2$— or O.

3. The compound according to claim 1 of the formula A:

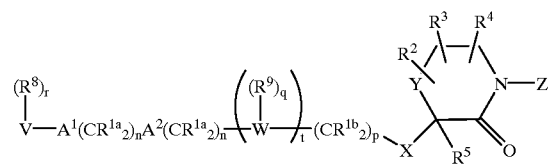

A wherein:
$R^{1a}$ is independently selected from: hydrogen or $C_1$–$C_6$ alkyl;
$R^{1b}$ is independently selected from:
a) hydrogen,
b) aryl, heterocycle, cycloalkyl, $R^{10}O$—, —$N(R^{10})_2$ or $C_2$–$C_6$ alkenyl,
c) unsubstituted or substituted $C_1$–$C_6$ alkyl wherein the substitutent on the substituted $C_1$–$C_6$ alkyl is selected from unsubstituted or substituted aryl, heterocycle, cycloalkyl, alkenyl, $R^{10}O$— and —$N(R^{10})_2$;
$R^3$ and $R^5$ are independently selected from H and $CH_3$;
$R^2$ and $R^4$ are independently selected from H;

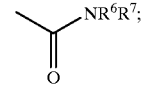

or $C_{1-5}$ alkyl, unbranched or branched, unsubstituted or substituted with one or more of:
1) aryl,
2) heterocycle,
3) $OR^6$,
4) $SR^{6a}$, $SO_2R^{6a}$, or
5)

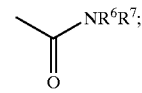

and any two of $R^2$, $R^3$, $R^4$, and $R^5$ are optionally attached to the same carbon atom;

$R^6$, $R^7$ and $R^{7a}$ are independently selected from:
  H; $C_{1-4}$ alkyl, $C_{3-6}$ cycloalkyl, aryl, heterocycle, unsubstituted or substituted with:
   a) $C_{1-4}$ alkoxy,
   b) halogen, or
   c) aryl or heterocycle;
$R^{6a}$ is selected from:
  $C_{1-4}$ alkyl or $C_{3-6}$ cycloalkyl, unsubstituted or substituted with:
   a) $C_{1-4}$ alkoxy,
   b) halogen, or
   c) aryl or heterocycle;
$R^8$ is independently selected from:
  a) hydrogen,
  b) $C_1-C_6$ alkyl, $C_2-C_6$ alkenyl, $C_2-C_6$ alkynyl, $C_1-C_6$ perfluoroalkyl, F, Cl, $R^{10}O$—, $R^{10}C(O)NR^{10}$—, CN, $NO_2$, $(R^{10})_2N$—$C(NR^{10})$—, $R^{10}C(O)$—, —$N(R^{10})_2$, or $R^{11}OC(O)NR^{10}$—, and
  c) $C_1-C_6$ alkyl substituted by $C_1-C_6$ perfluoroalkyl, $R^{10}O$—, $R^{10}C(O)NR^{10}$, $(R^{10})_2N$—$C(NR^{10})$—, $R^{11}C(O)$—, —$N(R^{10})_2$, or $R^{11}OC(O)NR^{10}$—;
$R^9$ is selected from:
  a) hydrogen,
  b) $C_2-C_6$ alkenyl, $C_2-C_6$ alkynyl, $C_1-C_6$ perfluoroalkyl, F, Cl, $R^{10}O$—, $R^{11}S(O)_m$—, $R^{10}C(O)NR^{10}$—, CN, $NO_2$, $(R^{10})_2N$—$C(NR^{10})$—, $R^{11}C(O)$—, —$N(R^{10})_2$, or $R^{11}OC(O)NR^{10}$—, and
  c) $C_1-C_6$ alkyl unsubstituted or substituted by $C_1-C_6$ perfluoroalkyl, F, Cl, $R^{10}O$—, $R^{11}S(O)_m$—, $R^{10}C(O)NR^{10}$—, CN, $(R^{10})_2N$—$C(NR^{10})$—, $R^{11}C(O)$—, —$N(R^{10})_2$, or $R^{11}OC(O)NR^{10}$—;
$R^{10}$ is independently selected from hydrogen, $C_1-C_6$ alkyl, benzyl and aryl;
$R^{11}$ is independently selected from $C_1-C_6$ alkyl and aryl;
$A^1$ and $A^2$ are independently selected from: a bond, —CH=CH—, —C≡C—, —C(O)—, —C(O)NR$^{10}$—, O, —N(R$^{10}$)—, or S(O)$_m$;
V is selected from:
  a) hydrogen,
  b) heterocycle selected from pyrrolidinyl, imidazolyl, pyridinyl, thiazolyl, pyridonyl, 2-oxopiperidinyl, indolyl, quinolinyl, isoquinolinyl, and thienyl,
  c) aryl,
  d) $C_1-C_{20}$ alkyl wherein from 0 to 4 carbon atoms are replaced with a a heteroatom selected from O, S, and N, and
  e) $C_2-C_{20}$ alkenyl, and
  provided that V is not hydrogen if $A^1$ is $S(O)_m$ and V is not hydrogen if $A^1$ is a bond, n is 0 and $A^2$ is $S(O)_m$;
W is a heterocycle selected from pyrrolidinyl, imidazolyl, pyridinyl, thiazolyl, pyridonyl, 2-oxopiperidinyl, indolyl, quinolinyl, or isoquinolinyl;
X is —CH$_2$— or —C(=O)—;
Y is a bond or —CH$_2$—;
Z is selected from:
  1) a unsubstituted or substituted group selected from aryl, heteroaryl, arylmethyl, heteroarylmethyl, arylsulfonyl, heteroarylsulfonyl, wherein the substituted group is substituted with one or more of the following:
   a) $C_{1-4}$ alkyl, unsubstituted or substituted with: $C_{1-4}$ alkoxy, $NR^6R^7$, $C_{3-6}$ cycloalkyl, aryl, heterocycle, HO, —S(O)$_m$R$^{6a}$, or —C(O)NR$^6$R$^7$,
   b) aryl or heterocycle,
   c) halogen,
   d) OR$^6$,
   e) NR$^6$R$^7$,
   f) CN,
   g) $NO_2$,
   h) CF$_3$;
   i) —S(O)$_m$R$^{6a}$,
   j) —C(O)NR$^6$R$^7$, or
   k) $C_3-C_6$ cycloalkyl; or
  2) unsubstituted $C_1-C_6$ alkyl, substituted $C_1-C_6$ alkyl, unsubstituted $C_3-C_6$ cycloalkyl or substituted $C_3-C_6$ cycloalkyl, wherein the substituted $C_1-C_6$ alkyl and substituted $C_3-C_6$ cycloalkyl is substituted with one or two of the following:
   a) $C_{1-4}$ alkoxy,
   b) $NR^6R^7$,
   c) $C_{3-6}$ cycloalkyl,
   d) —NR$^6$C(O)R$^7$,
   e) HO,
   f) —S(O)$_m$R$^{6a}$,
   g) halogen, or
   h) perfluoroalkyl;
m is 0, 1 or 2;
n is 0, 1, 2, 3 or 4;
p is 0, 1, 2, 3 or 4;
r is 0 to 5, provided that r is 0 when V is hydrogen;
t is 1; and
u is 4 or 5;
or a pharmaceutically acceptable salt thereof.

4. The compound according to claim 1 of the formula B:

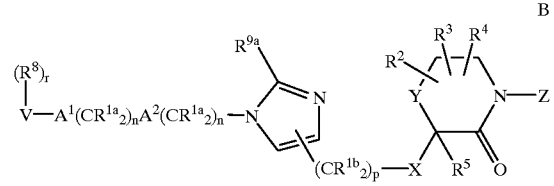

wherein:

$R^{1a}$ is selected from: hydrogen or $C_1-C_6$ alkyl;
$R^{1b}$ is independently selected from:
  a) hydrogen,
  b) aryl, heterocycle, cycloalkyl, $R^{10}O$—, —$N(R^{10})_2$ or $C_2-C_6$ alkenyl,
  c) $C_1-C_6$ alkyl unsubstituted or substituted by aryl, heterocycle, cycloalkyl, alkenyl, $R^{10}O$—, or —$N(R^{10})_2$;
$R^3$ and $R^5$ are independently selected from H and CH$_3$;
$R^2$ and $R^4$ are independently selected from H;

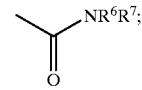

or $C_{1-5}$ alkyl, unbranched or branched, unsubstituted or substituted with one or more of:
  1) aryl,
  2) heterocycle,
  3) OR$^6$,
  4) SR$^{6a}$, SO$_2$R$^{6a}$, or

5)

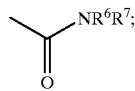

and any two of $R^2$, $R^3$, $R^4$, and $R^5$ are optionally attached to the same carbon atom;

$R^6$ and $R^7$ are independently selected from:
  a) hydrogen,
  b) $C_1$–$C_6$ alkyl, $C_2$–$C_6$ alkenyl, $C_2$–$C_6$ alkynyl, $C_1$–$C_6$ perfluoroalkyl, F, Cl, $R^{10}O$—, $R^{10}C(O)NR^{10}$—, CN, $NO_2$, $(R^{10})_2N$—$C(NR_{10})$—, $R^{10}C(O)$—, $R^{10}OC(O)$—, —$N(R^{10})_2$, or $R^{11}OC(O)NR^{10}$—, and
  c) $C_1$–$C_6$ alkyl substituted by $C_1$–$C_6$ perfluoroalkyl, $R^{10}O$—, $R^{10}C(O)NR^{10}$—, $(R^{10})_2N$—$C(NR^{10})$—, $R^{10}C(O)$—, $R^{10}OC(O)$—, —$N(R^{10})_2$, or $R^{11}OC(O)NR^{10}$—;

$R^{6a}$ is selected from:
$C_{1-4}$ alkyl or $C_{3-6}$ cycloalkyl, unsubstituted or substituted with:
  a) $C_{1-4}$ alkoxy,
  b) halogen, or
  c) aryl or heterocycle;

$R^8$ is independently selected from:
  a) hydrogen,
  b) $C_1$–$C_6$ alkyl, $C_2$–$C_6$ alkenyl, $C_2$–$C_6$ alkynyl, $C_1$–$C_6$ perfluoroalkyl, F, Cl, $R^{10}O$—, $R^{10}C(O)NR^{10}$—, CN, $NO_2$, $(R^{10})_2N$—$C(NR^{10})$—, $R^{10}C(O)$—, —$N(R^{10})_2$, or $R^{11}OC(O)NR^{10}$—, and
  c) $C_1$–$C_6$ alkyl substituted by $C_1$–$C_6$ perfluoroalkyl, $R^{10}O$—, $R^{10}C(O)NR^{10}$, $(R^{10})_2N$—$C(NR^{10})$—, $R^{10}C(O)$—, —$N(R^{10})_2$, or $R^{11}OC(O)NR_{10}$—;

$R^{9a}$ is hydrogen or methyl;

$R^{10}$ is independently selected from hydrogen, $C_1$–$C_6$ alkyl, benzyl and aryl;

$R^{11}$ is independently selected from $C_1$–$C_6$ alkyl and aryl;

$A^1$ and $A^2$ are independently selected from: a bond, —CH=CH—, —C≡C—, —C(O)—, —C(O)NR$^{10}$—, O, —N(R$^{10}$)—, or S(O)$_m$;

V is selected from:
  a) hydrogen,
  b) heterocycle selected from pyrrolidinyl, imidazolyl, pyridinyl, thiazolyl, pyridonyl, 2-oxopiperidinyl, indolyl, quinolinyl, isoquinolinyl, and thienyl,
  c) aryl,
  d) $C_1$–$C_{20}$ alkyl wherein from 0 to 4 carbon atoms are replaced with a a heteroatom selected from O, S, and N, and
  e) $C_2$–$C_{20}$ alkenyl, and
provided that V is not hydrogen if $A^1$ is $S(O)_m$ and V is not hydrogen if $A^1$ is a bond, n is 0 and $A^2$ is $S(O)_m$;

X is —$CH_2$— or —C(=O)—;

Y is a bond, —$CH_2$—, —NH—, —S(=O)$_m$— or O;

Z is selected from:
  1) a unsubstituted or substituted group selected from aryl, heteroaryl, arylmethyl, heteroarylmethyl, arylsulfonyl, heteroatrylsulfonyl, wherein the substituted group is substituted with one or more of the following:
    a) $C_{1-4}$ alkyl, unsubstituted or substituted with: $C_{1-4}$ alkoxy, $NR^6R^7$, $C_{3-6}$ cycloalkyl, aryl, heterocycle, HO, —$S(O)_mR^{6a}$, or —$C(O)NR^6R^7$,
    b) aryl or heterocycle,
    c) halogen,
    d) $OR^6$,
    e) $NR^6R^7$,
    f) CN,
    g) $NO_2$,
    h) $CF_3$;
    i) —$S(O)_mR^{6a}$,
    j) —$C(O)NR^6R^7$, or
    k) $C_3$–$C_6$ cycloalkyl; or
  2) unsubstituted $C_1$–$C_6$ alkyl, substituted $C_1$–$C_6$ alkyl, unsubstituted $C_3$–$C_6$ cycloalkyl or substituted $C_3$–$C_6$ cycloalkyl, wherein the substituted $C_1$–$C_6$ alkyl and substituted $C_3$–$C_6$ cycloalkyl is substituted with one or two of the following:
    a) $C_{1-4}$ alkoxy,
    b) $NR^6R^7$,
    c) $C_{3-6}$ cycloalkyl,
    d) —$NR^6C(O)R^7$,
    e) HO,
    f) —$S(O)_mR^{6a}$,
    g) halogen, or
    h) perfluoroalkyl;

m is 0, 1 or 2;
n is 0, 1, 2, 3 or 4;
p is 0, 1, 2, 3 or 4; and
r is 0 to 5, provided that r is 0 when V is hydrogen;
or a pharmaceutically acceptable salt thereof.

5. The compound according to claim 1 of the formula C:

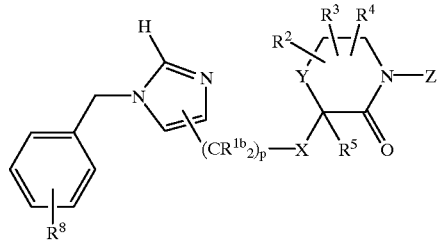

wherein:

$R^{1b}$ is independently selected from:
  a) hydrogen,
  b) aryl, heterocycle, cycloalkyl, $R^{10}O$—, —$N(R^{10})_2$ or $C_2$–$C_6$ alkenyl,
  c) $C_1$–$C_6$ alkyl unsubstituted or substituted by aryl, heterocycle, cycloalkyl, alkenyl, $R^{10}O$—, or —$N(R^{10})_2$;

$R^3$ and $R^5$ are independently selected from H and $CH_3$;
$R^2$ and $R^4$ are independently selected from H;

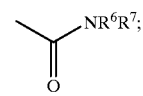

or $C_{1-5}$ alkyl, unbranched or branched, unsubstituted or substituted with one or more of:
  1) aryl,
  2) heterocycle,
  3) $OR^6$,
  4) $SR^{6a}$, $SO_2R^{6a}$, or

5)

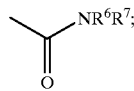

and any two of $R^2$, $R^3$, $R^4$, and $R^5$ are optionally attached to the same carbon atom;

$R^6$ and $R^7$ are independently selected from:
 a) hydrogen,
 b) $C_1$–$C_6$ alkyl, $C_2$–$C_6$ alkenyl, $C_2$–$C_6$ alkynyl, $C_1$–$C_6$ perfluoroalkyl, F, Cl, $R^{10}O$—, $R^{10}C(O)NR^{10}$—, CN, $NO_2$, $(R^{10})_2N$—$C(NR^{10})$—, $R^{11}C(O)$—, $R^{10}OC(O)$—, —$N(R^{10})_2$, or $R^{11}OC(O)NR^{10}$—, and
 c) $C_1$–$C_6$ alkyl substituted by $C_1$–$C_6$ perfluoroalkyl, $R^{10}O$—, $R^{10}C(O)NR^{10}$, $(R^{10})_2N$—$C(NR^{10})$—, $R^{10}C(O)$—, $R^{10}OC(O)$—, —$N(R^{10})_2$, or $R^{11}OC(O)NR^{10}$—;

$R^{6a}$ is selected from:
 $C_{1-4}$ alkyl or $C_{3-6}$ cycloalkyl, unsubstituted or substituted with:
 a) $C_{1-4}$ alkoxy,
 b) halogen, or
 c) aryl or heterocycle;

$R^8$ is independently selected from:
 a) hydrogen,
 b) $C_1$–$C_6$ alkyl, $C_2$–$C_6$ alkenyl, $C_2$–$C_6$ alkynyl, $C_1$–$C_6$ perfluoroalkyl, F, Cl, $R^{10}O$—, $R^{10}C(O)NR^{10}$—, CN, $NO_2$, $(R^{10})_2N$—$C(NR^{10})$—, $R^{10}C(O)$—, —$N(R^{10})_2$, or $R^{11}OC(O)NR^{10}$—, and
 c) $C_1$–$C_6$ alkyl substituted by $C_1$–$C_6$ perfluoroalkyl, $R^{10}O$—, $R^{10}C(O)NR^{10}$, $(R^{10})_2N$—$C(NR^{10})$—, $R^{10}C(O)$—, $R^{10}OC(O)$—, —$N(R^{10})_2$, or $R^{11}OC(O)NR^{10}$—;

$R^{10}$ is independently selected from hydrogen, $C_1$–$C_6$ alkyl, benzyl and aryl;

$R^{11}$ is independently selected from $C_1$–$C_6$ alkyl and aryl;

X is —$CH_2$— or —$C(=O)$—;

Y is a bond, —$CH_2$—, —NH—, —$S(=O)_m$— or O;

Z is selected from:
 1) a unsubstituted or substituted group selected from aryl, heteroaryl, arylmethyl, heteroarylmethyl, arylsulfonyl, heteroarylsulfonyl, wherein the substituted group is substituted with one or more of the following:
  a) $C_{1-4}$ alkyl, unsubstituted or substituted with: $C_{1-4}$ alkoxy, $NR^6R^7$, $C_{3-6}$ cycloalkyl, aryl, heterocycle, HO, —$S(O)_mR^{6a}$, or —$C(O)NR^6R^7$,
  b) aryl or heterocycle,
  c) halogen,
  d) $OR^6$,
  e) $NR^6R^7$,
  f) CN,
  g) $NO_2$,
  h) $CF_3$;
  i) —$S(O)_mR^{6a}$,
  j) —$C(O)NR^6R^7$, or
  k) $C_3$–$C_6$ cycloalkyl; or
 2) unsubstituted $C_1$–$C_6$ alkyl, substituted $C_1$–$C_6$ alkyl, unsubstituted $C_3$–$C_6$ cycloalkyl or substituted $C_3$–$C_6$ cycloalkyl, wherein the substituted $C_1$–$C_6$ alkyl and substituted $C_3$–$C_6$ cycloalkyl is substituted with one or two of the following:
  a) $C_{1-4}$ alkoxy,
  b) $NR^6R^7$,
  c) $C_{3-6}$ cycloalkyl,
  d) —$NR^6C(O)R^7$,
  e) HO,
  f) —$S(O)_mR^{6a}$,
  g) halogen, or
  h) perfluoroalkyl;

m is 0, 1 or 2; and
p is 0, 1, 2, 3 or 4;
or a pharmaceutically acceptable salt thereof.

6. The compound according to claim 1 of the formula D:

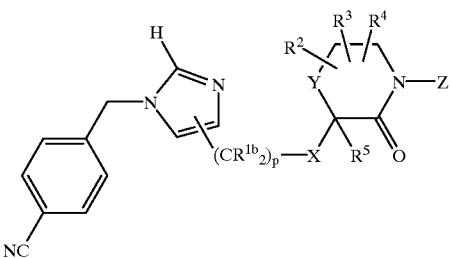

D wherein:
$R^{1b}$ is independently selected from:
 a) hydrogen,
 b) aryl, heterocycle, cycloalkyl, $R^{10}O$—, —$N(R^{10})_2$ or $C_2$–$C_6$ alkenyl,
 c) $C_1$–$C_6$ alkyl unsubstituted or substituted by aryl, heterocycle, cycloalkyl, alkenyl, $R^{10}O$—, or —$N(R^{10})_2$;

$R^2$ and $R^4$ are independently selected from: hydrogen or $C_1$–$C_6$ alkyl;
$R^3$ and $R^5$ are hydrogen;

$R^6$ and $R^7$ are independently selected from:
 a) hydrogen,
 b) $C_1$–$C_6$ alkyl, $C_2$–$C_6$ alkenyl, $C_2$–$C_6$ alkynyl, $C_1$–$C_6$ perfluoroalkyl, F, Cl, $R^{10}O$—, $R^{10}C(O)NR^{10}$—, CN, $NO_2$, $(R^{10})_2N$—$C(NR^{10})$—, $R^{10}C(O)$—, $R^{10}OC(O)$—, —$N(R^{10})_2$, or $R^{11}OC(O)NR^{10}$—, and
 c) $C_1$–$C_6$ alkyl substituted by $C_1$–$C_6$ perfluoroalkyl, $R^{10}O$—, $R^{10}C(O)NR^{10}$, $(R^{10})_2N$—$C(NR^{10})$—, $R^{10}C(O)$—, $R^{10}OC(O)$—, —$N(R^{10})_2$, or $R^{11}OC(O)NR^{10}$—;

$R^{10}$ is independently selected from hydrogen, $C_1$–$C_6$ alkyl, benzyl and aryl;

$R^{11}$ is independently selected from $C_1$–$C_6$ alkyl and aryl;

X is —$CH_2$— or —$C(=O)$—;

Y is a bond, —$CH_2$—, —NH—, —$S(=O)_m$— or O;

Z is mono- or bicyclic aryl, mono- or bicyclic heteroaryl, mono- or bicyclic arylmethyl, mono- or bicyclic heteroarylmethyl, mono- or bicyclic arylsulfonyl, mono- or bicyclic heteroarylsulfonyl, unsubstituted or substituted with one or two of the following:
 1) $C_{1-4}$ alkyl, unsubstituted or substituted with:
  a) $C_{1-4}$ alkoxy,
  b) $NR^6R^7$,
  c) $C_{3-6}$ cycloalkyl,
  d) aryl or heterocycle,
  e) HO,
  f) —$S(O)_mR^6$, or
  g) —$C(O)NR^6R^7$,
 2) aryl or heterocycle,
 3) halogen,
 4) $OR^6$,
 5) $NR^6R^7$,
 6) CN,
 7) $NO_2$, 8) CF$_3$;
9) —S(O)$_m$R$^6$,
10) —C(O)NR$^6$R$^7$, or
11) C$_3$–C$_6$ cycloalkyl;

m is 0, 1 or 2; and
p is 0, 1, 2, 3 or 4;
or the pharmaceutically acceptable salts thereof.

7. A compound which inhibits farnesyl-protein transferase which is:

N-[2-{1-(4-Cyanobenzyl)-5-imidazolyl}ethyl]-3-carbamoyl-1-phenyl-2-piperidinone

3-[3-{1-(4-Cyanobenzyl)-5-imidazolyl}-1-propyl]-1-phenyl-2-piperidinone

3-[3-{1-(4-Cyanobenzyl)-5-imidazolyl}-1-propyl]-1-phenyl-2-pyrrolidinone (±)cis—3-[3-{1-(4-Cyanobenzyl)-5-imidazolyl}-1-propyl]-4-methoxymethyl-1-phenyl-2-pyrrolidinone (±)trans-3-[3-{1-(4-Cyanobenzyl)-5-imidazolyl}-1-propyl]-4-methoxymethyl-1-phenyl-2-pyrrolidinone 3-[2-{5-(4-Cyanobenzyl)-1-imidazolyl}-1-ethyl]-1-phenyl-2-pyrrolidinone 1-Benzyl-3-[2-{5-(4-cyanobenzyl)-1-imidazolyl-1-ethyl]-2-pyrrolidinone or (±)-1-(3-chloropheny)-3-[1-(1-(4-cyanobenzyl)-5-imidazolyl)-1-(hydroxy)methyl]-2-piperazinone or a pharmaceutically acceptable salt or optical isomer thereof.

8. The compound according to claim 7 which is:
N-[2-(1-(4-Cyanobenzyl)-5-imidazolyl}ethyl]-3-carbamoyl-1-phenyl-2-piperidinone

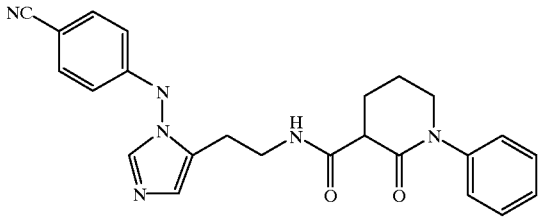

or a pharmaceutically acceptable salt or optical isomer thereof.

9. The compound according to claim 7 which is:
3-[2-{5-(4-Cyanobenzyl)-1-imidazolyl}-1-ethyl]-1-phenyl-2-pyrrolidinone

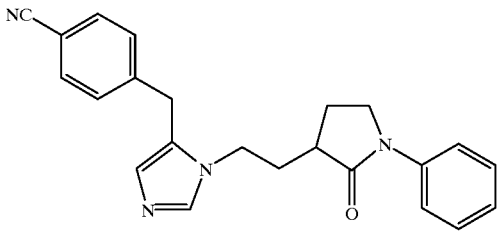

or a pharmaceutically acceptable salt or optical isomer thereof.

10. The compound according to claim 7 which is:
1-Benzyl-3-[2-{5-(4-cyanobenzyl)-1-imidazolyl}-1-ethyl]-2-pyrrolidinone

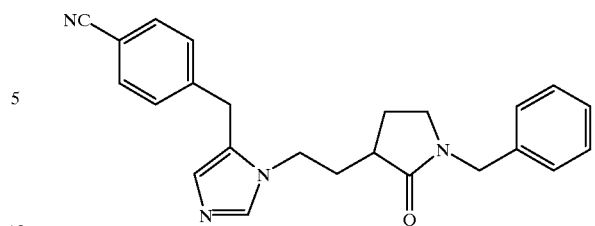

or a pharmaceutically acceptable salt or optical isomer thereof.

11. A pharmaceutical composition comprising a pharmaceutical carrier, and dispersed therein, a therapeutically effective amount of a compound of claim 1.

12. A pharmaceutical composition comprising a pharmaceutical carrier, and dispersed therein, a therapeutically effective amount of a compound of claim 3.

13. A pharmaceutical composition comprising a pharmaceutical carrier, and dispersed therein, a therapeutically effective amount of a compound of claim 4.

14. A pharmaceutical composition comprising a pharmaceutical carrier, and dispersed therein, a therapeutically effective amount of a compound of claim 7.

15. A method for inhibiting farnesyl-protein transferase which comprises administering to a mammal in need thereof a therapeutically effective amount of a composition of claim 11.

16. A method for inhibiting farnesyl-protein transferase which comprises administering to a mammal in need thereof a therapeutically effective amount of a composition of claim 12.

17. A method for inhibiting farnesyl-protein transferase which comprises administering to a mammal in need thereof a therapeutically effective amount of a composition of claim 13.

18. A method for inhibiting farnesyl-protein transferase which comprises administering to a mammal in need thereof a therapeutically effective amount of a composition of claim 14.

19. A method for treating cancer which comprises administering to a mammal in need thereof a therapeutically effective amount of a composition of claim 11.

20. A method for treating cancer which comprises administering to a mammal in need thereof a therapeutically effective amount of a composition of claim 12.

21. A method for treating cancer which comprises administering to a mammal in need thereof a therapeutically effective amount of a composition of claim 13.

22. A method for treating cancer which comprises administering to a mammal in need thereof a therapeutically effective amount of a composition of claim 14.

23. A method for treating neurofibromin benign proliferative disorder which comprises administering to a mammal in need thereof a therapeutically effective amount of a composition of claim 11.

24. A method for treating blindness related to retinal vascularization which comprises administering to a mammal in need thereof a therapeutically effective amount of a composition of claim 11.

25. A method for treating infections from hepatitis delta and related viruses which comprises administering to a mammal in need thereof a therapeutically effective amount of a composition of claim 10.

26. A method for preventing restenosis which comprises administering to a mammal in need thereof a therapeutically effective amount of a composition of claim 11.

27. A method for treating polycystic kidney disease which comprises administering to a mammal in need thereof a therapeutically effective amount of a composition of claim 11.

28. A pharmaceutical composition made by combining the compound of claim 1 and a pharmaceutically acceptable carrier.

29. A process for making a pharmaceutical composition comprising combining a compound of claim 1 and a pharmaceutically acceptable carrier.

* * * * *

UNITED STATES PATENT AND TRADEMARK OFFICE
CERTIFICATE OF CORRECTION

PATENT NO. : 6,001,835      Page 1 of 3
DATED     : December 14, 1999
INVENTOR(S) : Christopher J. Dinsmore and Theresa M. Williams It is certified that error appears in the above-identified patent and that said Letters Patent is hereby corrected as shown below:

In Claim 1, column 57, line 2 should read as follows:
-- $NO_2$, $R^{10}C(O)$-, $N_3$, -$N(R^{10})_2$, or $R^{11}OC(O)NR$ --.

In Claim 1, column 57, line 41, remove the following:
-- 5) –$NR^6R^7$ --.

In Claim 1, column 59, line 4 should read as follows:
-- $C_2$-$C_6$ alkynyl, perfluoroalkyl, F, Cl, Br, $R^{10}O$-, $R^{11}S$ --.

In Claim 1, column 59, line 13 should read as follows:
-- or $R^{10}OC(O)NH$-; --.

In Claim 1, column 59, line 20 should read as follows:
-- -$N(R^{10})_2$, or $R^{11}OC(O)NR^{10}$-, and --.

In Claim 3, column 61, line 22 should read as follows:
-- $R^{10}O$-, $R^{10}C(O)NR^{10}$-, $(R^{10})_2N$-$C(NR^{10})$-, $R^{10}C$ --.

In Claim 3, column 61, line 29 should read as follows:
-- $NO_2$, $(R^{10})_2N$-$C(NR^{10})$-, $R^{10}C(O)$-, -$N(R^{10})_2$, or --.

In Claim 4, column 63, line 36 should read as follows:
-- $C(O)$-, -$N(R^{10})_2$, or $R^{11}OC(O)NR^{10}$-; --.

In Claim 4, column 63, line 62, the first word should read as following:
-- heteroarylsulfonyl --.

UNITED STATES PATENT AND TRADEMARK OFFICE
CERTIFICATE OF CORRECTION

PATENT NO. : 6,001,835
DATED : December 14, 1999
INVENTOR(S) : Christopher J. Dinsmore and Theresa M. Williams It is certified that error appears in the above-identified patent and that said Letters Patent is hereby corrected as shown below:

In claim 5, column 65, line 15 should read as follows:
-- $-N(R^{10})_2$, or $R^{11}OC(O)NR^{10}-$, and --.

In claim 5, column 65, line 34 should read as follows:
-- $R^{10}O-$, $R^{10}C(O)NR^{10}-$, $(R^{10})_2N-C(NR^{10})-$, $R^{10}C$ --.

In claim 8, column 67, line 32 should read as follows:
-- N-[2-{1-(4-Cyanobenzyl)-5-imidazolyl}ethyl]-3- --.

UNITED STATES PATENT AND TRADEMARK OFFICE
CERTIFICATE OF CORRECTION

Page 3 of 3

PATENT NO. : 6,001,835
DATED : December 14, 1999
INVENTOR(S) : Christopher J. Dinsmore and Theresa M. Williams It is certified that error appears in the above-identified patent and that said Letters Patent is hereby corrected as shown below:

In Claim 8, column 67, the structure between lines 35-44 should read as follows:

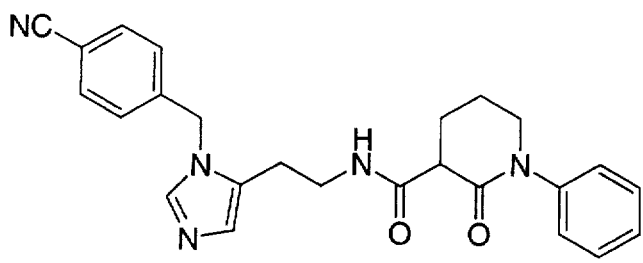

Signed and Sealed this

Twenty-first Day of November, 2000

*Attest:*

Q. TODD DICKINSON

*Attesting Officer*      *Director of Patents and Trademarks*